(12) United States Patent
Ball et al.

(10) Patent No.: US 9,045,527 B2
(45) Date of Patent: Jun. 2, 2015

(54) SMALL MOLECULE CONJUGATES WITH DIMETAL SPECIES FOR PROTEIN INHIBITION

(71) Applicant: WILLIAM MARSH RICE UNIVERSITY, Houston, TX (US)

(72) Inventors: Zachary T. Ball, Houston, TX (US); Rituparna Kundu, Houston, TX (US); Brian V. Popp, Houston, TX (US); Dean R. Madden, Hanover, NH (US); Patrick R. Cushing, Hanover, NH (US)

(73) Assignees: WILLIAM MARSH RICE UNIVERSITY, Houston, TX (US); TRUSTEES OF DARTMOUTH COLLEGE, Hanover, NH (US)

( * ) Notice: Subject to any disclaimer, the term of this patent is extended or adjusted under 35 U.S.C. 154(b) by 56 days.

(21) Appl. No.: 13/916,359

(22) Filed: Jun. 12, 2013

(65) Prior Publication Data

US 2014/0011983 A1  Jan. 9, 2014

Related U.S. Application Data

(60) Provisional application No. 61/658,760, filed on Jun. 12, 2012.

(51) Int. Cl.
*C07K 7/00* (2006.01)
*C07K 14/435* (2006.01)
*C07H 21/00* (2006.01)
*C07K 1/107* (2006.01)
*A61K 47/48* (2006.01)

(52) U.S. Cl.
CPC ............... *C07K 1/1075* (2013.01); *C07K 1/107* (2013.01); *A61K 47/48015* (2013.01)

(58) Field of Classification Search
None
See application file for complete search history.

(56) References Cited

U.S. PATENT DOCUMENTS 8,415,292 B2 *  4/2013  Madden et al. ................ 514/1.8
8,476,407 B2 *  7/2013  Ball et al. ...................... 530/326

* cited by examiner

*Primary Examiner* — Karlheinz R Skowronek
*Assistant Examiner* — Mindy Newman
(74) *Attorney, Agent, or Firm* — Robert R. Riddle; Reed Smith LLP

(57) ABSTRACT

Methods for targeting a protein by providing an inhibitor covalently linked to a rhodium(II) complex, introducing the inhibitor to the target protein and allowing the inhibitor and protein to interact. The rhodium(II) complex covalently linked to the inhibitor binds the target protein both inorganically and organically and forms stabilizing secondary contacts between the rhodium(II) complex and the protein.

5 Claims, 26 Drawing Sheets

Thermal Denaturation of Metallopeptide coiled coils

| entry | sequence | E3X | $T_m$ (°C) |
|---|---|---|---|
| 1 | | $E3_gF$ | 39.5 |
| 2 | | $E3_gE$ | 50.2 |
| 3 | | $E3_gH$ | 66.1 |
| 4[b] | | $E3_gH$ +50 mM imid. | 46.0 |
| 5 | | $E3_gM$ | >75 |
| 6[c] | | $E3_gM$ | 70.4 |
| 7 | | $E3_gC$ | 33.5 |
| 8 | | $E3_cH$ | 47.0 |

| entry | peptide | sequence | $K_i$ (µM) | |
|---|---|---|---|---|
| 1 | 1 | VQDTRL | 320 | ± 43 |
| 2 | 1-Rh | VQ*TRL | 6.3[b] | ± 0.7 |
| 3 | 2 | QLDVTR | >500 | |
| 4 | 2-Rh | QL*VTR | 10.0[b] | ± 0.9 |
| 5 | 3 | EWPTSII | 65 | ± 5 |
| 6 | 3-Rh | *WPTSII | 1.7[c] | ± 0.2 |
| 7 | 4 | EVQSTRL | 42 | ± 5 |
| 8 | 4-Rh | *VQSTRL | 0.56[c] | ± 0.08 |

Metallopeptide ligands for PDZ domains

| sequence | N1P1 affinity (uM) | | CALP affinity (uM) | | H301A | | |
|---|---|---|---|---|---|---|---|
| VQDTRL | 0.70 | | 297 ±44 | | | | |
| *VQDTRL | | | ~49 | | | | |
| EVQSTRL | 0.71 ±0.04 | ⟩22x | 41 ±2 | ⟩95x | 89 | ±3 | ⟩8x |
| *EVQSTRL | 0.032 ±0.005 | | 0.43 ±0.02 | | 11.3 | ±0.7 | |
| EVQSTRI | | | 171 ±7 | ⟩380x | 375 | ±67 | ⟩30x |
| *EVQSTRI | | | 0.45 ±0.14 | | 12.3 | ±0.0 | |
| EWPTSII | >500 | | 114 ±7 | ⟩88x | | | |
| *EWPTSII | >50 | | 1.30 ±0.01 | | | | |
| EVQSTRF | 1.9 ±0.1 | ⟩13x | >1,000 | | | | |
| *EVQSTRF | 0.15 ±0.05 | | >15 | | | | |

His301

$T_m$ = 44.4±0.4 °C
$K_d^{25°C}$ = 11±1 µM
$K_d^{37°C}$ = 68±7 µM

| entry | [imidazole], mM | Tm (°C) |
|---|---|---|
| 1 | 0 | 66.0 |
| 2 | 5 | 63.9 |
| 3 | 10 | 58.5 |
| 4 | 20 | 60.1 |
| 5 | 30 | 56.8 |
| 6 | 40 | 61.0 |
| 7 | 50 | 46.0 |
| 8 | 100 | 46.5 |

| entry | pH | Tm (°C) |
|---|---|---|
| 1 | 4.3 | 56.9 |
| 2 | 5.3 | 63.4 |
| 3 | 5.9 | 66.0 |
| 4 | 6.6 | 66.0 |
| 5 | 7.2 | 61.8 |
| 6 | 7.6 | 55.9 |

SEQUENCE LISTING

```
<160> NUMBER OF SEQ ID NOS: 24

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      inhibitor peptide

<400> SEQUENCE: 1

Val Gln Asp Thr Arg Leu
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      inhibitor peptide
<220> FEATURE:
<221> NAME/KEY: MOD_RES
<222> LOCATION: (3)..(3)
<223> OTHER INFORMATION: Residue modified with a rhodium(II) side-chain
      complex

<400> SEQUENCE: 2

Val Gln Asp Thr Arg Leu
1               5

<210> SEQ ID NO 3
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      inhibitor peptide

<400> SEQUENCE: 3

Gln Leu Asp Val Thr Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      inhibitor peptide
<220> FEATURE:
<221> NAME/KEY: MOD_RES
<222> LOCATION: (3)..(3)
<223> OTHER INFORMATION: Residue modified with a rhodium(II) side-chain
      complex

<400> SEQUENCE: 4

Gln Leu Asp Val Thr Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      inhibitor peptide

<400> SEQUENCE: 5

Glu Trp Pro Thr Ser Ile Ile
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      inhibitor peptide

<400> SEQUENCE: 6

Glu Val Gln Ser Thr Arg Leu
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      inhibitor peptide
<220> FEATURE:
<221> NAME/KEY: MOD_RES
<222> LOCATION: (1)..(1)
<223> OTHER INFORMATION: Residue modified with a rhodium(II) side-chain
      complex

<400> SEQUENCE: 7

Glu Val Gln Ser Thr Arg Leu
1               5
```

-continued

```
<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      inhibitor peptide
<220> FEATURE:
<221> NAME/KEY: MOD_RES
<222> LOCATION: (1)..(1)
<223> OTHER INFORMATION: Residue modified with a rhodium(II) side-chain
      complex

<400> SEQUENCE: 8

Glu Trp Pro Thr Ser Ile Ile
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      inhibitor peptide
<220> FEATURE:
<221> NAME/KEY: MOD_RES
<222> LOCATION: (7)..(7)
<223> OTHER INFORMATION: Residue modified with a rhodium(II) side-chain
      complex

<400> SEQUENCE: 9

Glu Val Gln Ser Thr Arg Leu
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      inhibitor peptide
<220> FEATURE:
<221> NAME/KEY: MOD_RES
<222> LOCATION: (6)..(6)
<223> OTHER INFORMATION: Residue modified with a rhodium(II) side-chain
      complex

<400> SEQUENCE: 10

Val Gln Asp Thr Arg Leu
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      inhibitor peptide
<220> FEATURE:
<221> NAME/KEY: MOD_RES
<222> LOCATION: (7)..(7)
<223> OTHER INFORMATION: Residue modified with a rhodium(II) side-chain
      complex

<400> SEQUENCE: 11

Glu Trp Pro Thr Ser Ile Ile
1               5

<210> SEQ ID NO 12
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      inhibitor peptide

<400> SEQUENCE: 12

Glu Val Gln Ser Thr Arg Ile
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      inhibitor peptide
<220> FEATURE:
<221> NAME/KEY: MOD_RES
<222> LOCATION: (1)..(1)
<223> OTHER INFORMATION: Residue modified with a rhodium(II) side-chain
      complex

<400> SEQUENCE: 13

Glu Val Gln Ser Thr Arg Ile
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      inhibitor peptide

<400> SEQUENCE: 14

Glu Val Gln Ser Thr Arg Phe
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      inhibitor peptide
<220> FEATURE:
<221> NAME/KEY: MOD_RES
<222> LOCATION: (1)..(1)
<223> OTHER INFORMATION: Residue modified with a rhodium(II) side-chain
      complex

<400> SEQUENCE: 15

Glu Val Gln Ser Thr Arg Phe
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      inhibitor peptide
<220> FEATURE:
<221> NAME/KEY: MOD_RES
<222> LOCATION: (6)..(6)
<223> OTHER INFORMATION: Residue modified with a rhodium(II) side-chain
      complex

<400> SEQUENCE: 16

Gln Leu Asp Val Thr Arg
```

```
<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      inhibitor peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Residue modified with a rhodium(II) side-chain
      complex
<220> FEATURE:
<223> OTHER INFORMATION: C-term OH

<400> SEQUENCE: 17

Glu Val Gln Ser Thr Arg Leu
1               5

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Residue modified with a rhodium(II) side-chain
      complex
<220> FEATURE:
<221> NAME/KEY: MOD_RES
<222> LOCATION: (13)..(13)
<223> OTHER INFORMATION: Residue modified with a rhodium(II) side-chain
      complex

<400> SEQUENCE: 18

Lys Ile Ser Ala Leu Lys Gln Lys Glu Ser Ala Leu Glu Gln Lys Ile
1               5                   10                  15

Ser Ala Leu Glu Lys
            20

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid

<400> SEQUENCE: 19

Glu Ile Ser Ala Leu Glu Lys Xaa Ile Ser Ala Leu Glu Gln Glu Ile
1               5                   10                  15

Ser Ala Leu Glu Lys
            20

<210> SEQ ID NO 20
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 20

Glu Ile Ser Ala Leu Glu Lys Glu Ile Ser His Leu Glu Gln Glu Ile
1               5                   10                  15

Ser Ala Leu Glu Lys
            20

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      inhibitor peptide
<220> FEATURE:
<221> NAME/KEY: MOD_RES
<222> LOCATION: (3)..(3)
<223> OTHER INFORMATION: Residue modified with a rhodium(II) side-chain
      complex
<220> FEATURE:
<221> NAME/KEY: MOD_RES
<222> LOCATION: (6)..(6)
<223> OTHER INFORMATION: Residue modified with a rhodium(II) side-chain
      complex

<400> SEQUENCE: 21

Val Gln Asp Thr Arg Leu
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      inhibitor peptide
<220> FEATURE:
<221> NAME/KEY: MOD_RES
<222> LOCATION: (1)..(1)
<223> OTHER INFORMATION: Residue modified with a rhodium(II) side-chain
      complex
<220> FEATURE:
<221> NAME/KEY: MOD_RES
<222> LOCATION: (7)..(7)
<223> OTHER INFORMATION: Residue modified with a rhodium(II) side-chain
      complex

<400> SEQUENCE: 22

Glu Val Gln Ser Thr Arg Leu
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      inhibitor peptide
<220> FEATURE:
<221> NAME/KEY: MOD_RES
<222> LOCATION: (3)..(3)
<223> OTHER INFORMATION: Residue modified with a rhodium(II) side-chain
      complex
<220> FEATURE:
<221> NAME/KEY: MOD_RES
<222> LOCATION: (6)..(6)
<223> OTHER INFORMATION: Residue modified with a rhodium(II) side-chain
      complex

<400> SEQUENCE: 23
```

```
Gln Leu Asp Val Thr Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      inhibitor peptide
<220> FEATURE:
<221> NAME/KEY: MOD_RES
<222> LOCATION: (1)..(1)
<223> OTHER INFORMATION: Residue modified with a rhodium(II) side-chain
      complex
<220> FEATURE:
<221> NAME/KEY: MOD_RES
<222> LOCATION: (7)..(7)
<223> OTHER INFORMATION: Residue modified with a rhodium(II) side-chain
      complex

<400> SEQUENCE: 24

Glu Trp Pro Thr Ser Ile Ile
1               5
```

SMALL MOLECULE CONJUGATES WITH DIMETAL SPECIES FOR PROTEIN INHIBITION

CROSS-REFERENCE TO RELATED APPLICATION

This application claims the benefit of U.S. Provisional Application No. 61/658,760 filed Jun. 12, 2012, which is incorporated by reference.

STATEMENT OF GOVERNMENT INTEREST

This invention was made with government support under Grant Nos. R21-NS067613 and R01-DK075309 awarded by National Institute of Health. The government has certain rights in the invention.

BACKGROUND

Protein-protein interactions (PPIs) often play key roles in cellular processes and human disease. Examples of biological events that involve PPIs include signal transduction, transcription, protein ligand-receptor interactions, and protein assembly. There are many instances in which it is therapeutically useful to block the interaction of a target protein with another protein or with a therapeutic agent (e.g., small molecule drug). Protein inhibition is the most common and successful target for drug treatment. However, the proteins involved in these interactions often lack compact pockets accessible to traditional ligand-discovery methods.

The instant application contains a Sequence Listing which has been submitted electronically in ASCII format and is hereby incorporated by reference in its entirety. Said ASCII copy, created on Jan. 6, 2015, is named 13-21054-US_SL.txt and is 8,225 bytes in size.

SUMMARY

The present disclosure generally relates to methods for providing protein inhibition and more particularly to methods using protein inhibitors comprising rhodium(II) complexes. The rhodium(II) complex(es) disclosed herein are alternatively referred to as rhodium(II) metallopeptides. Accordingly, the terms "rhodium(II) metallopeptides" and "rhodium(II) complex(es)" are interchangeable for the purposes of the current invention.

The features and advantages of the present disclosure will be apparent to those skilled in the art. While numerous changes may be made by those skilled in the art, such changes are within the spirit of the invention.

DRAWINGS

Some specific example embodiments of the disclosure may be understood by referring, in part, to the following description and the accompanying drawings.

FIG. 1 discloses "Ac-E$^{Rh}$VQSTRL-OH" as SEQ ID NO: 17.

Figures 3, 4:
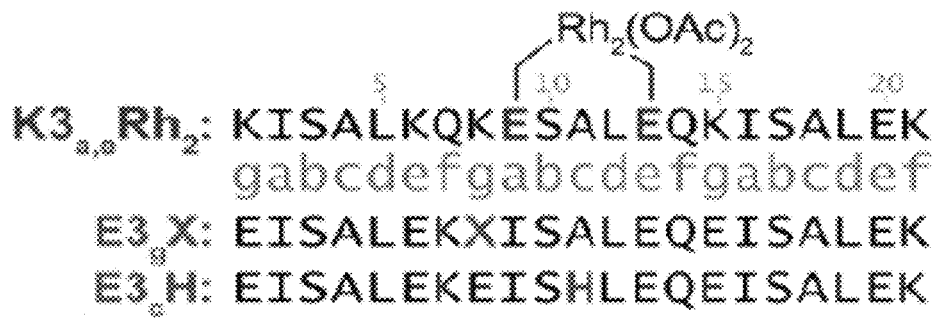
FIG. 3 depicts representative sequences (SEQ ID NOS 18-20, respectively, in order of appearance) used. The lower case letters represent positions on a helical-wheel depiction.

FIG. 4 is a table detailing the thermal denaturation of metallopeptide coiled coils. The following standard conditions: equimolar mixtures of E3X and K3$_{a,e}$Rh$_2$ in aq buffer (pH 5.9-6.2) were monitored by CD (222 nm) from −5 to 95° C. at 1° C./min. The peptide concentrations are 100 μM. The CD monitored is at 225 nm and in certain embodiments, the peptide concentration is 33 μM.

Figure 5:
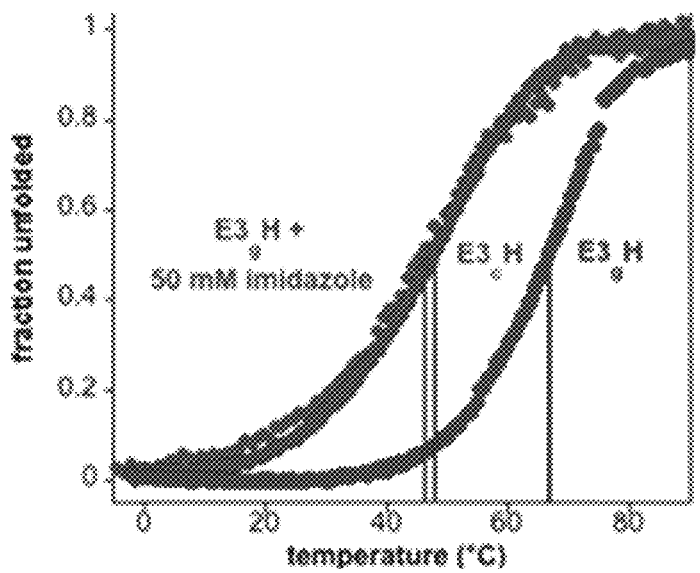

FIG. 5 is a graph showing selection of thermal denaturation profiles for stoichiometric mixtures of E3H and K3$_{a,e}$Rh$_2$. Vertical lines indicate melting temperature (TO.

Figure 6:
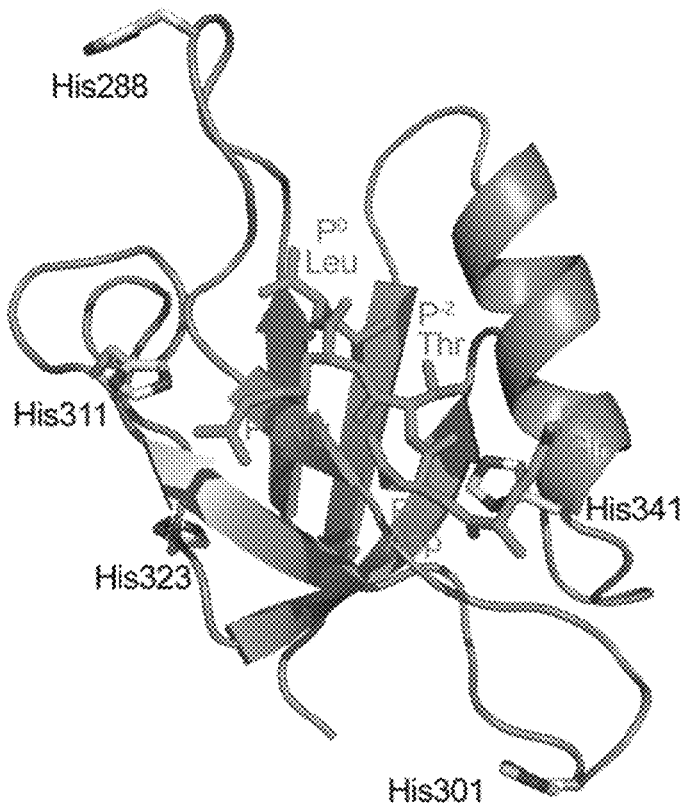

FIG. 6 is an illustration of the structure of the CAL PDZ domain. All CALP Histidine side chains are also shown.

Figure 7:
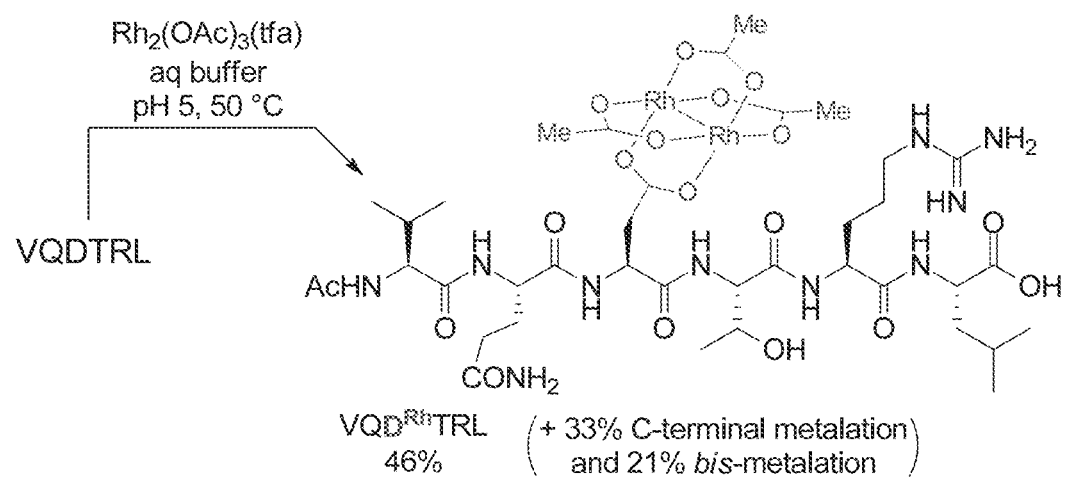

FIG. 7 is an illustration of the synthesis of a PDZ-binding metallopeptide; VQDTRL (SEQ ID NO:1), VQD$^{Rh}$TRL (SEQ ID NO:2).

Figure 8:
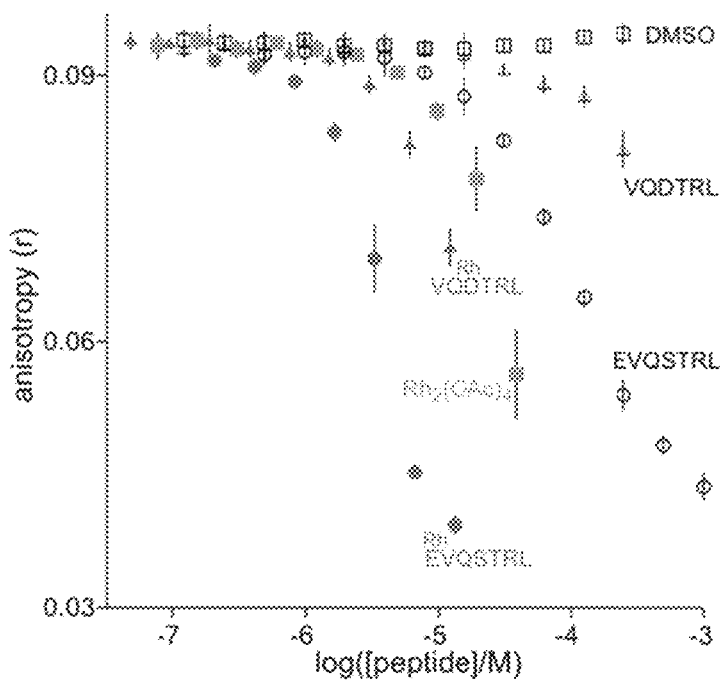

FIG. 8 is a graph of fluorescence anisotropy displacement isotherms for candidate CALP inhibitors; VQDTRL (SEQ ID NO:1), VQD$^{Rh}$TRL (SEQ ID NO:2), EVQSTRL (SEQ ID NO:6), E$^{Rh}$VQSTRL (SEQ ID NO:7).

Figures 9A, 9B:
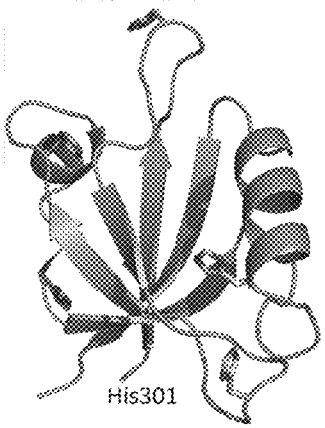

FIG. 9A is a table of metallopeptide inhibitors of CALP. [a], inhibitor equilibrium dissociation ($K_i$) constants were determined for cognate peptide/metallopeptide pairs. In embodiment [b] rhodium(II) complexes, including Rh$_2$(OAc)$_4$ ($K_i$=13±5 μM) exhibit nonspecific inhibition, establishing an upper bound for these measurements. In embodiment, [c] $K_i$ value significantly different from Rh$_2$(OAc)$_4$ (p<0.05, n=3). VQDTRL (SEQ ID NO:1); VQD$^{Rh}$TRL (SEQ ID NO:2); QLDVTR (SEQ ID NO:3); QLD$^{Rh}$VTR (SEQ ID NO:4); EWPTSII (SEQ ID NO:5); E$^{Rh}$WPTSII (SEQ ID NO:8); EVQSTRL (SEQ ID NO:6); E$^{Rh}$VQSTRL (SEQ ID NO:7).

FIG. 9B is a table of metallopeptide inhibitors of CALP, N1P1, and H301A; VQDTRL (SEQ ID NO:1), VQD$^{Rh}$TRL (SEQ ID NO:2), EVQSTRL (SEQ ID NO:6), E$^{Rh}$VQSTRL (SEQ ID NO:7), EVQSTRI (SEQ ID NO:12), E$^{Rh}$VQSTRI (SEQ ID NO:13), EWPTSII (SEQ ID NO:5), E$^{Rh}$WPTSII (SEQ ID NO:8), EVQSTRF (SEQ ID NO:14), E$^{Rh}$VQSTRF (SEQ ID NO:15).

Figure 10A:

FIG. 10A is a western blot of native CAL captured from epithelial lysates in the presence of increasing concentrations of EVQSTRL (SEQ ID NO:6) peptide with (+Rh) or without (−Rh) rhodium.

Figure 10B:
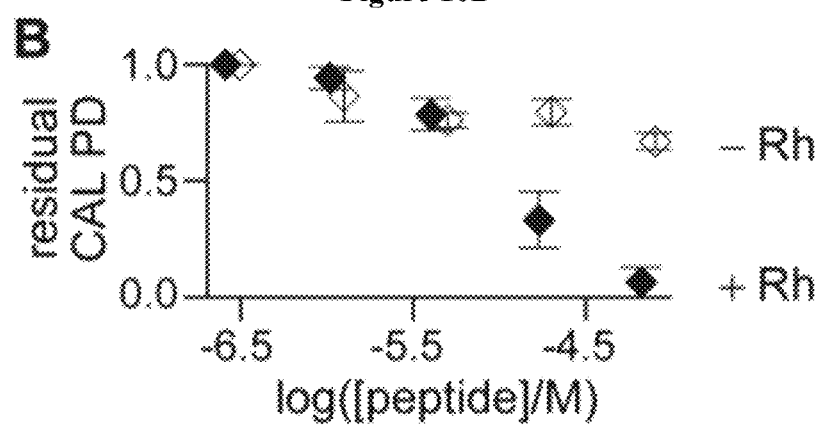

FIG. 10B is a graph of residual CAL PD. Quantification reveals dose-dependent inhibition of CAL pulldown (PD) by the metalated peptide.

Figure 11:
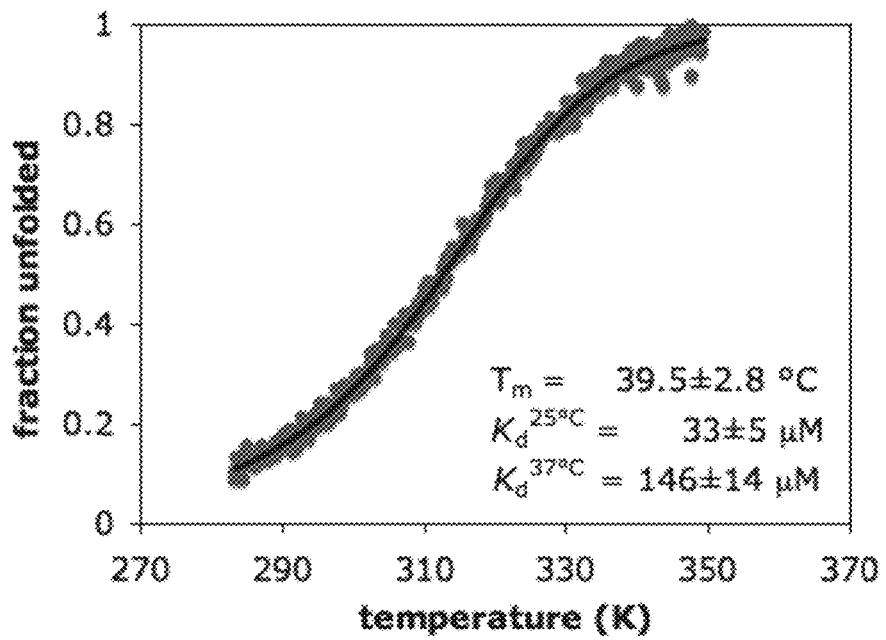

FIG. 11 depicts the thermal denaturation profile of E3$_g$F-K3$_{a,e}$Rh$_2$([peptide]$_{total}$=200 μM).

Figure 12:
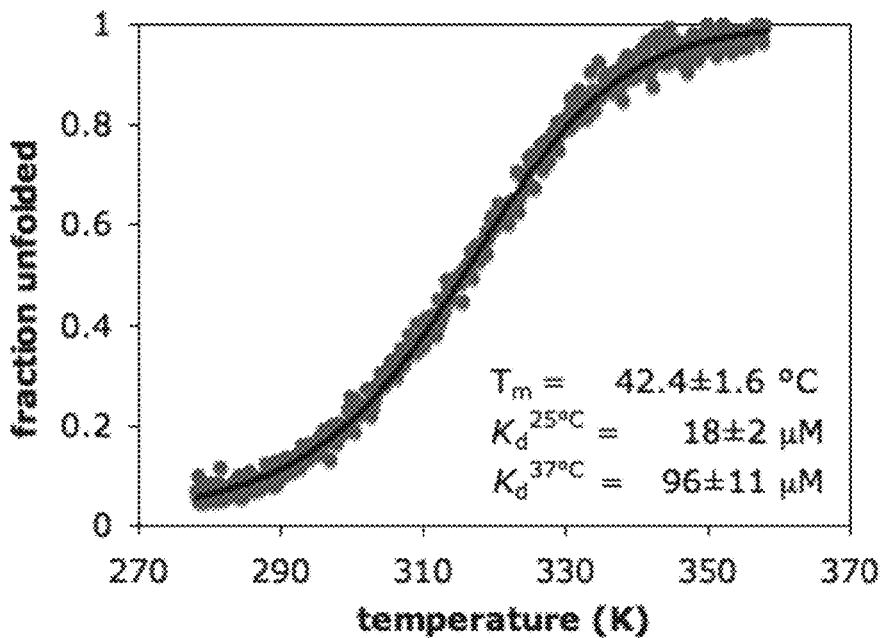

FIG. 12 depicts the thermal denaturation profile of E3gY-K3a,eRh2 ([peptide]total=200 μM).

Figure 13:
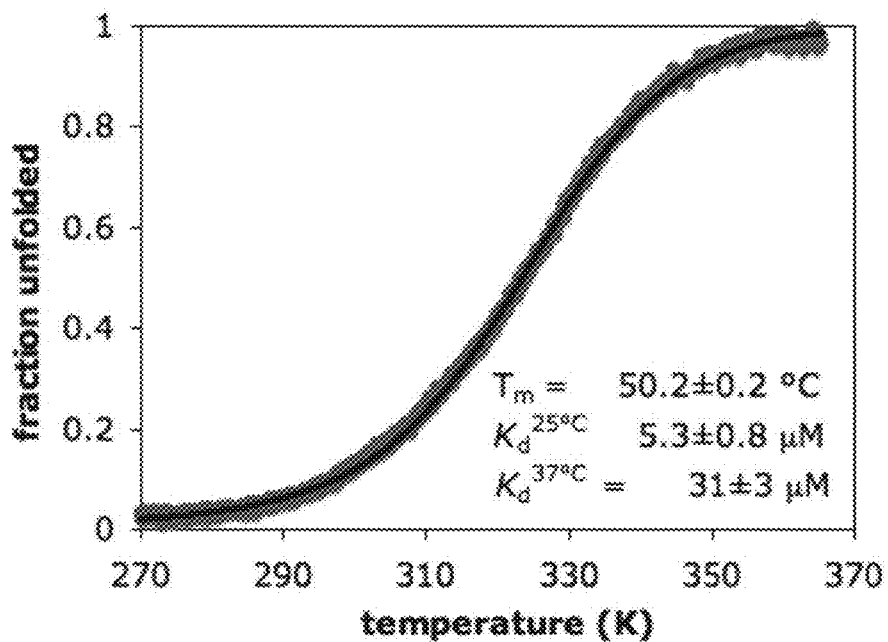

FIG. 13 depicts the thermal denaturation profile of E3gE-K3a,eRh2 ([peptide]total=200 μM)

Figure 14:
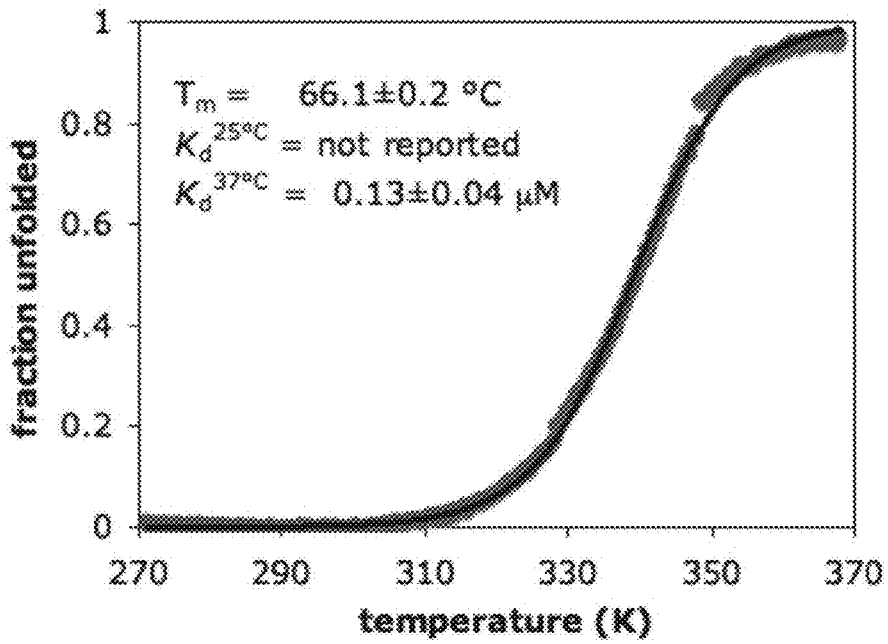

FIG. 14 depicts the thermal denaturation profile of E3gH-K3a,eRh2 ([peptide]total=200 μM)

Figure 15:
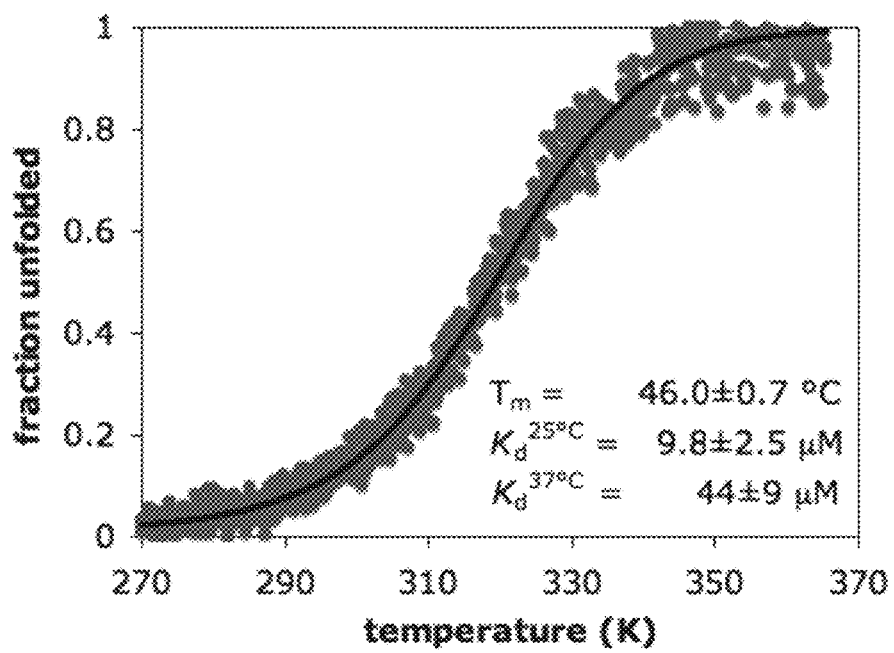
Figure 16:
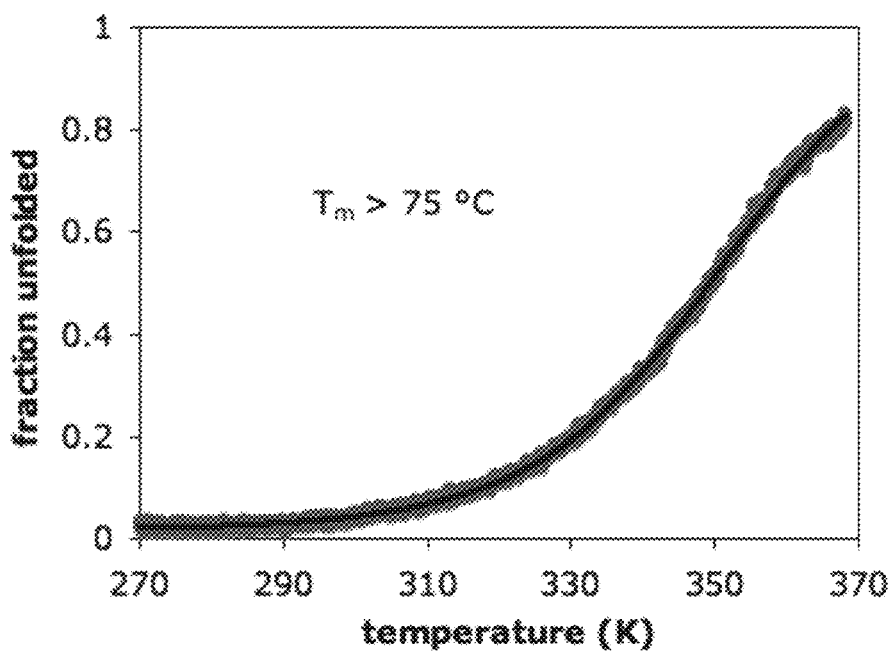

FIG. 15 depicts the thermal denaturation profile of E3gH-K3a,eRh2([peptide]total=200 μM)+50 mM imidazole FIG. 16 depicts the thermal denaturation profile of E3gM-K3a,eRh2 ([peptide]total=200 μM).

Figure 17:
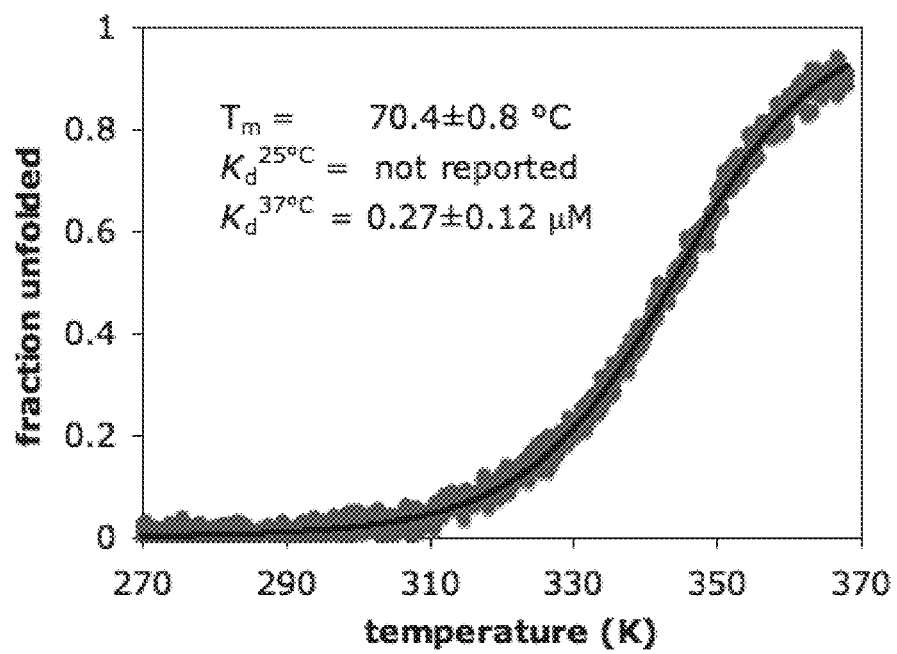

FIG. 17 depicts the thermal denaturation profile of E3gM-K3a,eRh2 ([peptide]total=66 μM).

Figure 18:
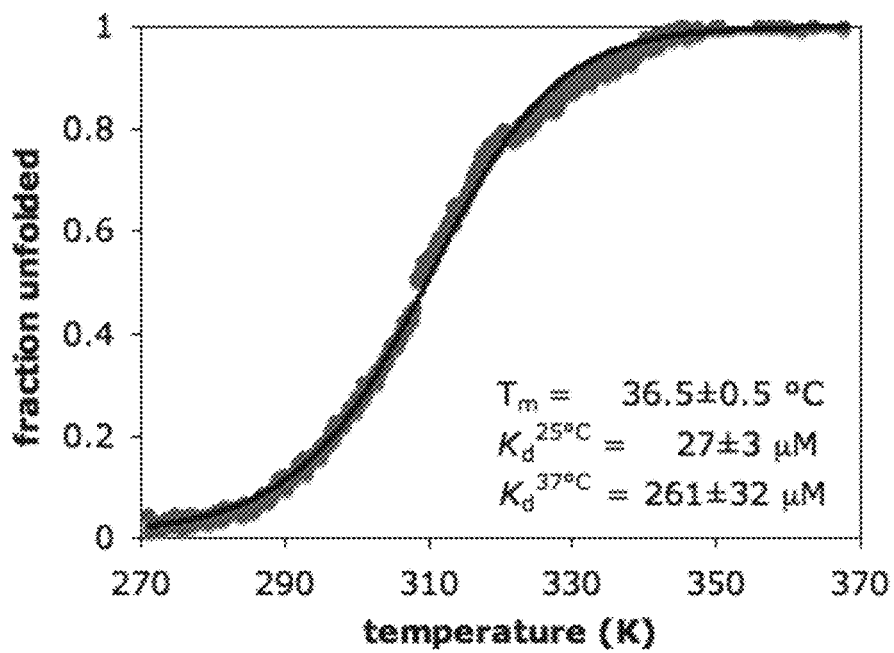

FIG. 18 depicts the thermal denaturation profile of E3gC-K3a,eRh2 ([peptide]total=200 μM).

Figures 19, 20:
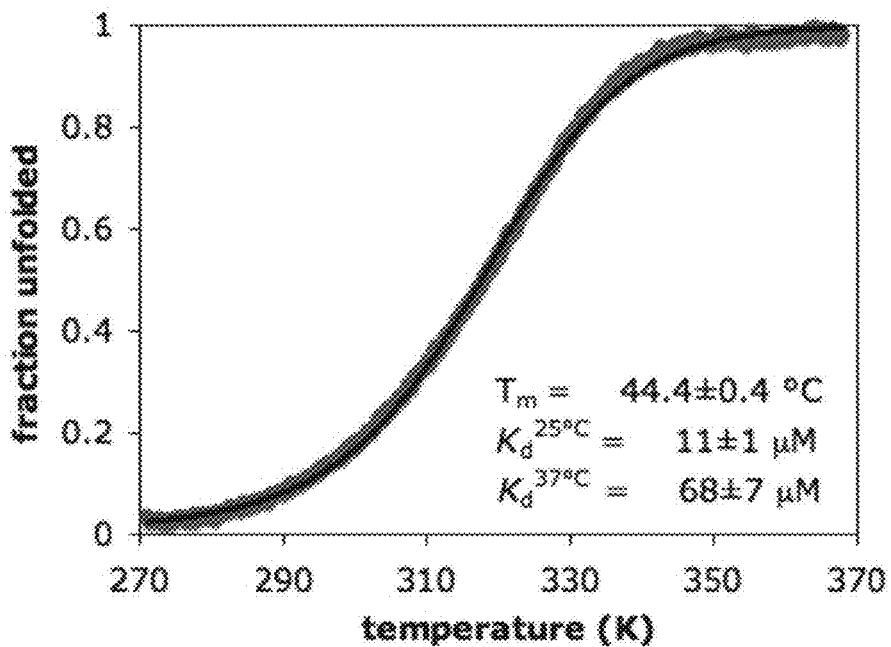

FIG. 19 depicts the thermal denaturation profile of E3cH-K3a,eRh2 ([peptide]total=200 μM)

FIG. 20 illustrates the stability of E3gH-K3a,eRh2 assembly ([peptide]total=200 μM) in aq buffer at pH 5.8 with increasing concentration of imidazole. The Tm values are determined by thermal denaturation using CD absorption at 222 nm.

Figures 21, 22:
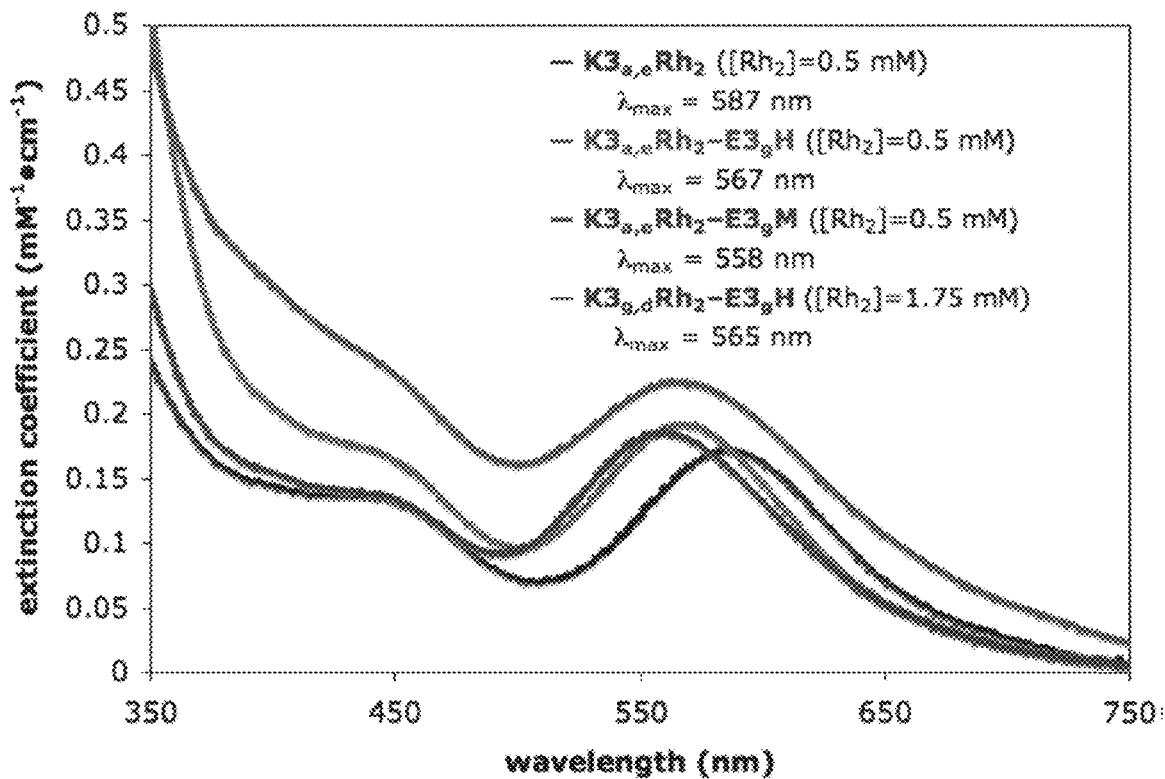

FIG. 21 illustrates the stability of E3gH-K3a,eRh2 assembly ([peptide]total=200 μM) in aq buffer at varying pH (4.3-7.6). The Tm values are determined by thermal denaturation using CD absorption at 222 nm.

FIG. 22 is an illustration of the visible absorption spectra of dirhodium-metallopeptide assemblies. (A) K3a,eRh2 [black trace], (B) K3a,eRh2-E3gH [red trace], (C) K3a,eRh2-E3gH [blue trace], (D) K3g,dRh2-E3gH [purple trace]. Sample preparation: 1:1 mixture of metallopeptide and E3-peptide with (A-C) aq buffer at pH 6.2 and (D) aq KOH at pH~7.0.

Figure 23:
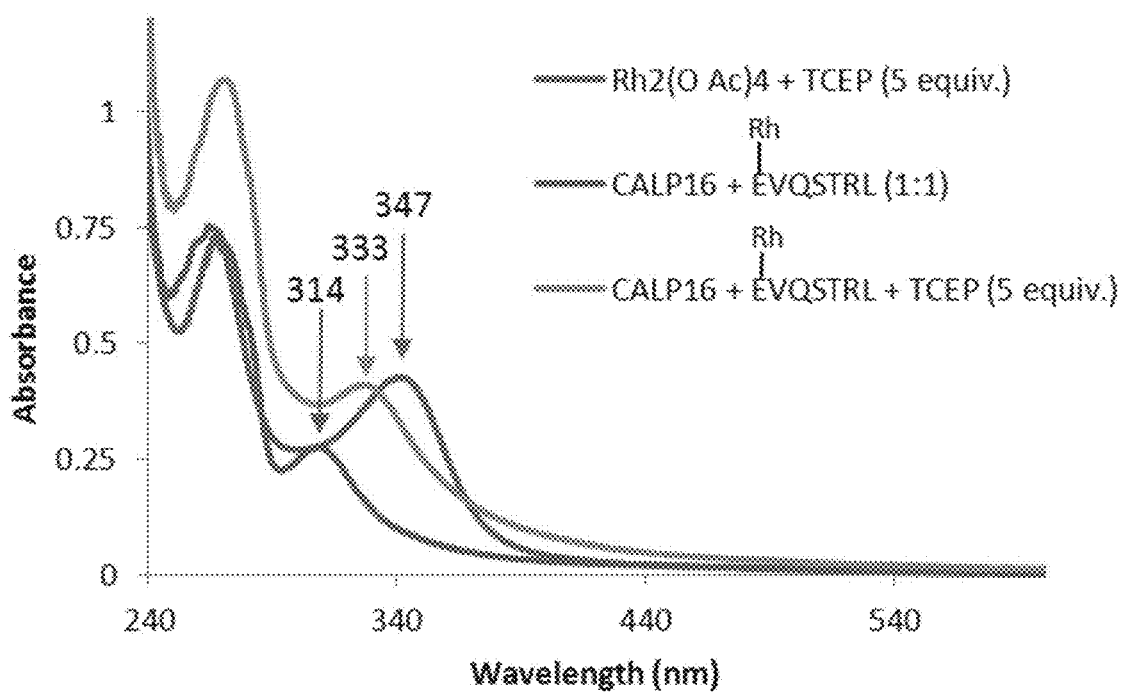

FIG. 23 depicts the comparison of UV-Vis spectrum of $Rh_2(OAc)_4$ after addition of TCEP (5 equiv.) with that of 1:1 mixture of CALP16 and $E^{Rh}$VQSTRL (SEQ ID NO:7) before and after addition of TCEP (5 equiv).

Figure 24:
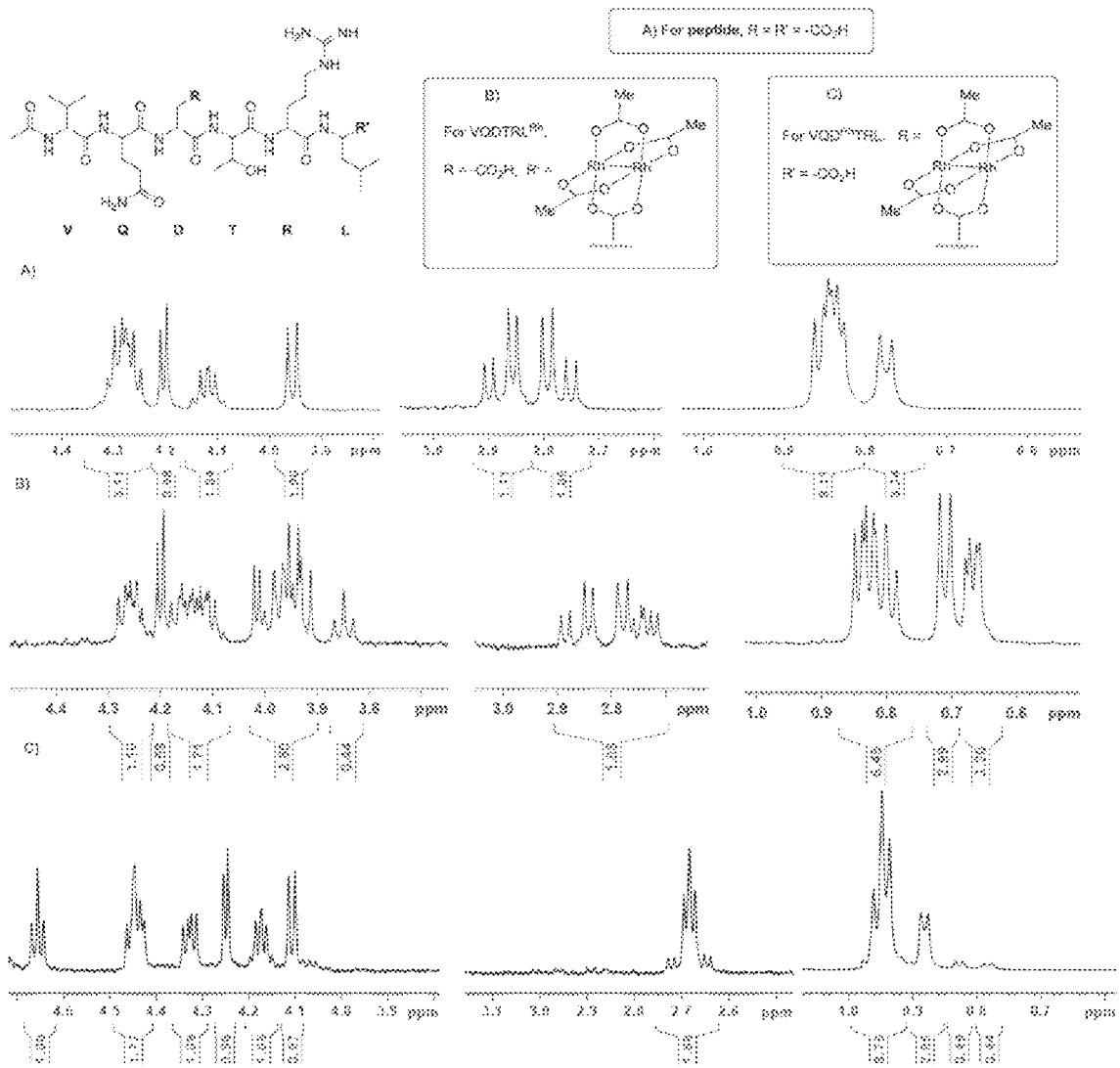

FIG. 24 depicts the NMR comparison of (A) VQDTRL (SEQ ID NO:1) peptide B) VQDTRL$^{Rh}$ (SEQ ID NO:10) and C) VQD$^{Rh}$TRL (SEQ ID NO:2). Dirhodium attachment results in changes to one leucine Hδ methyl (from 0.87 ppm to 0.65 ppm, Δδ1H ca. −0.22 ppm) in the C-terminal bound product VQDTRL$^{Rh}$ (SEQ ID NO:10) (A vs B) and to the aspartate Hβ methylene (from 2.81 ppm to 2.69 ppm, Δδ1H ca. −0.12 ppm) in the side-chain-bound metallopeptide VQD$^{Rh}$TRL (SEQ ID NO:2) (A vs C). Synthesis of $E^{Rh}$-VQSTRL (SEQ ID NO:7). This complex was prepared similarly to that of VQD$^{Rh}$TRL (SEQ ID NO:2), using 2 mg of EVQSTRL (SEQ ID NO:6) peptide affording a blue solid (1.1 mg, 38% yield).

Figure 25:
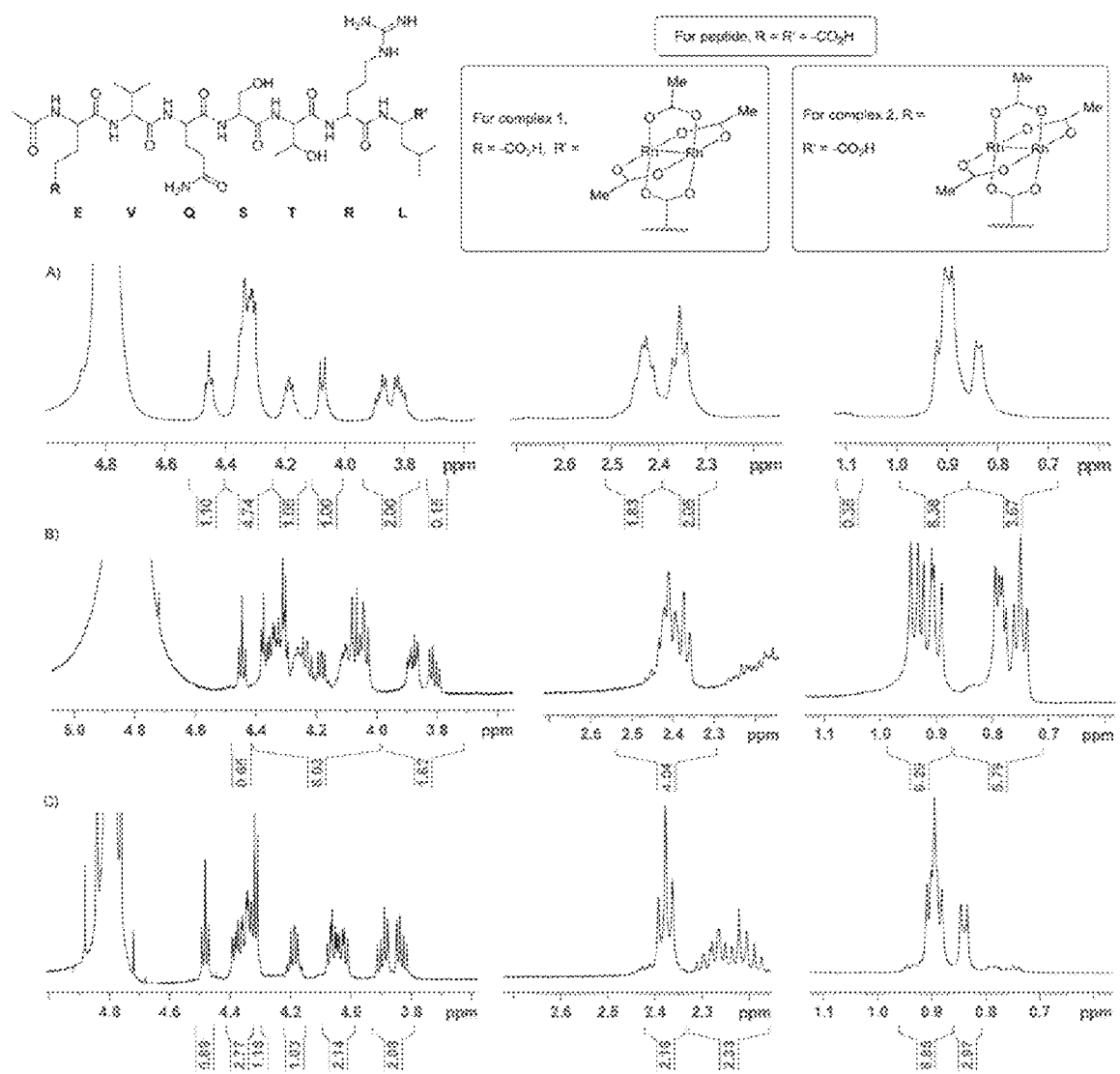

FIG. 25 depicts the NMR comparison of (A) EVQSTRL (SEQ ID NO:6) peptide B) EVQSTRL$^{Rh}$ (SEQ ID NO:9) and C) $E^{Rh}$VQSTRL (SEQ ID NO:7). Dirhodium attachment resulted in upfield shift of one leucine Hδ methyl (from ~0.9 ppm to 0.75 ppm, Δδ1H ca. −0.15 ppm) in the C-terminal bound product EVQSTRL$^{Rh}$ (SEQ ID NO:9) (A vs B), and of the glutamate Hδ methylene from 2.45 ppm to 2.2 ppm, Δδ1H ca. −0.15 ppm, in the side-chain-bound metallopeptide, $E^{Rh}$-VQSTRL (SEQ ID NO:7) (A vs C). Synthesis of QLD$^{Rh}$VTR (SEQ ID NO:4). This complexation was performed similarly to that of VQD$^{Rh}$TRL (SEQ ID NO:2), on 1.9 mg of QLDVTR (SEQ ID NO:3) peptide affording a blue solid (1.0 mg, 37% yield).

Figure 26:
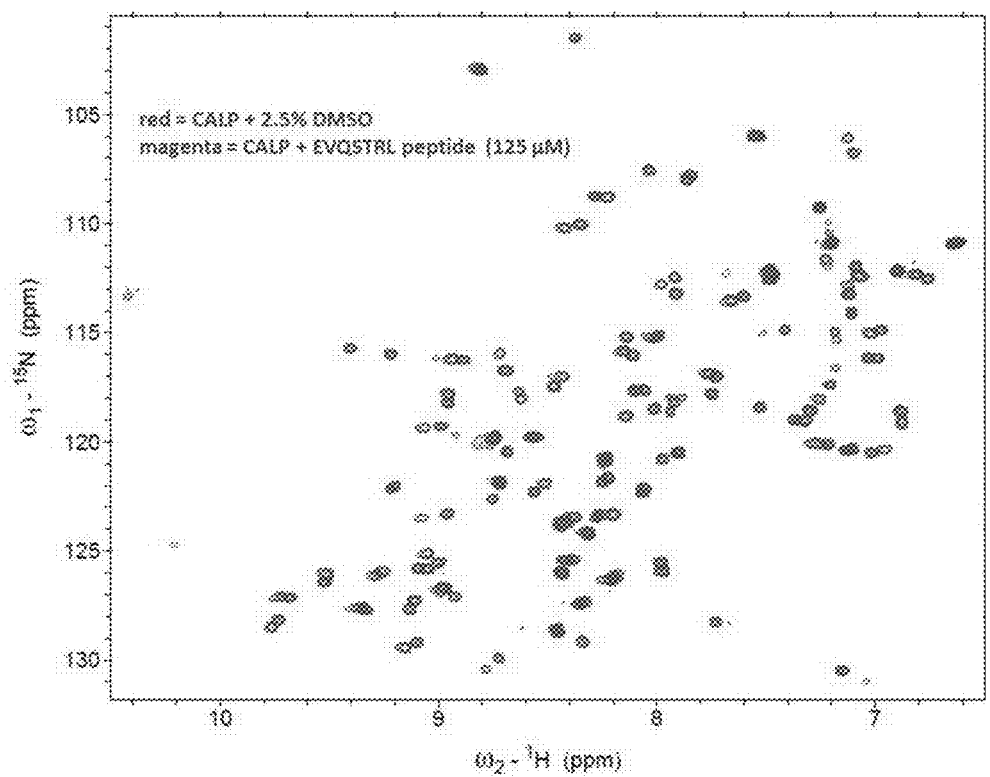

FIG. 26 is a depiction of the HSQC spectra of 15N-CALP determined separately (red) and in the presence of 125-μM EVQSTRL (SEQ ID NO:6) peptide (magenta) in 2.5% (v/v) DMSO.

Figure 27:
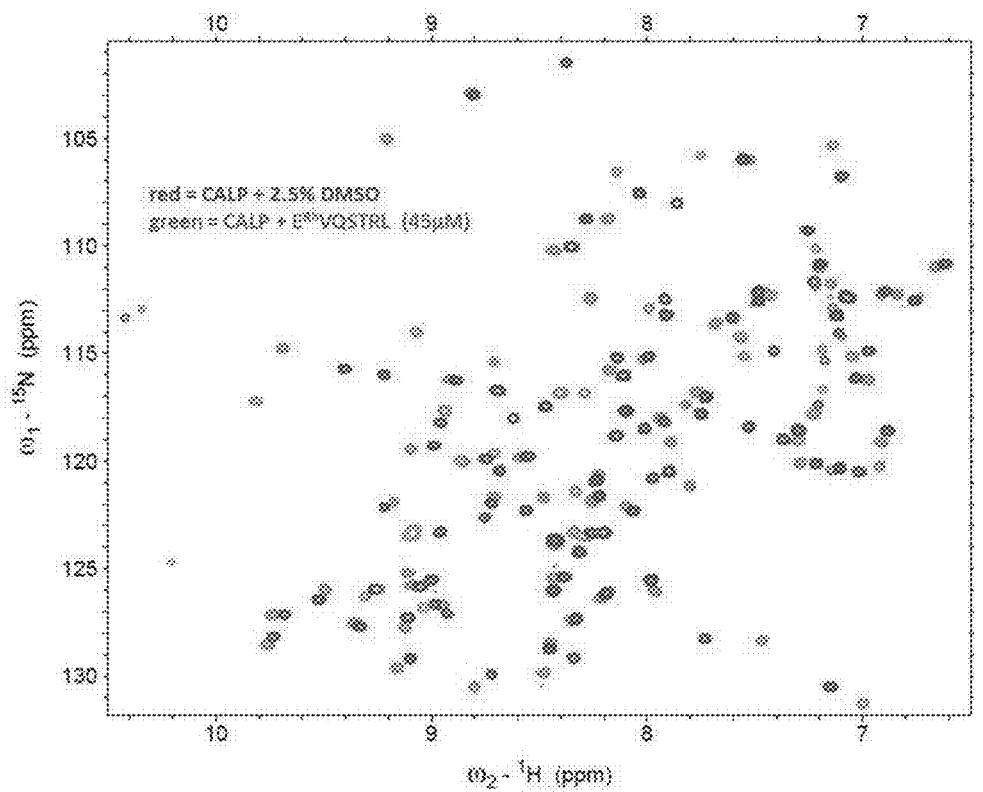

FIG. 27 illustrates that EVQSTRL (SEQ ID NO:6) and $E^{Rh}$VQSTRL (SEQ ID NO:7) are competitive inhibitors of the CAL PDZ domain. HSQC spectra of 15N-CALP determined separately (red) and in the presence of 125-μM $E^{Rh}$-VQSTRL (SEQ ID NO:7) metallopeptide (green) in 2.5% (v/v) DMSO.

Figure 28:
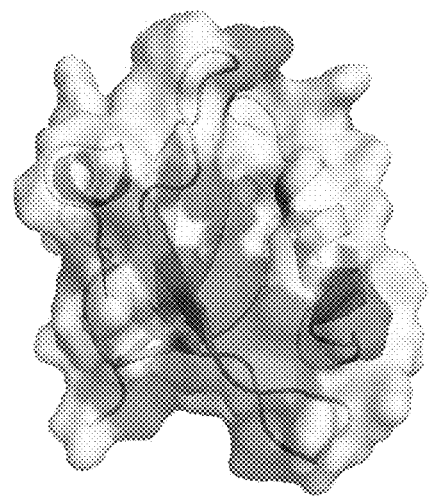

FIG. 28 is a surface representation of the CAL PDZ domain (PDB entry 2DC2; grey) shows the interfaces associated with EVQSTRL (SEQ ID NO:6) binding (red; δ norm>0.2 ppm) and with the localized differences observed between the metalated and non-metalated sequences (magenta). The interface is consistent with the position of the canonical PDZ binding cleft and overlaps with previously reported binding surfaces.

Figure 29A:
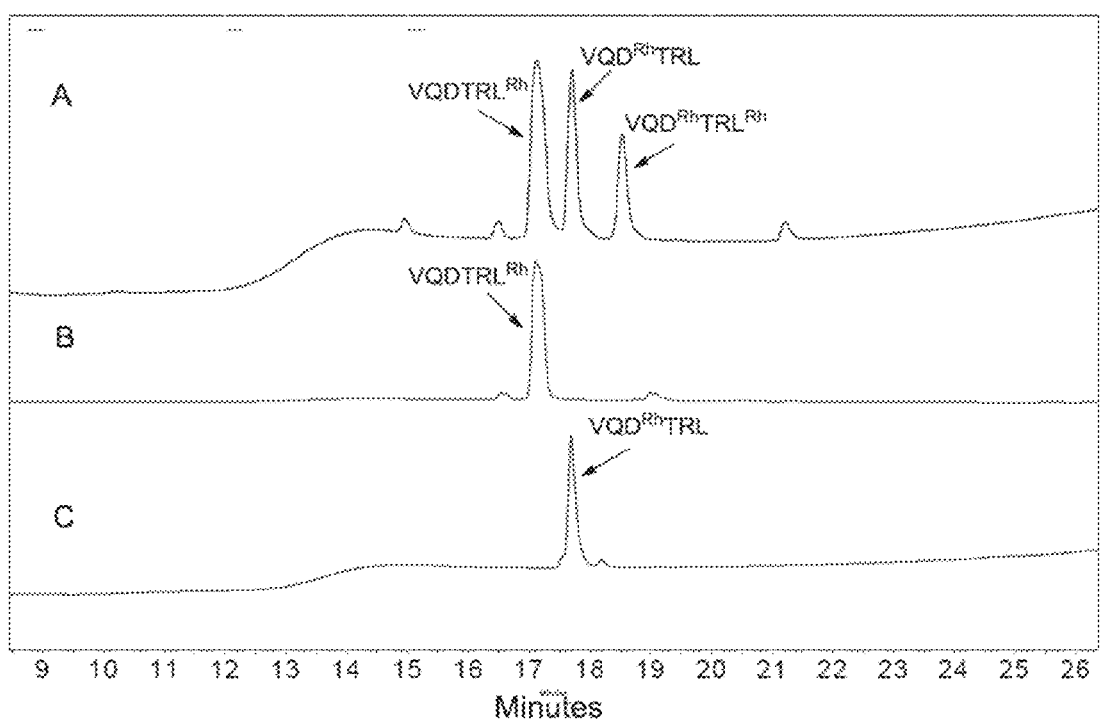

FIG. 29A illustrates the HPLC traces of (A) crude metalation (SEQ ID NOS 10, 2 and 21, respectively, in order of appearance) (B) pure VQDTRL$^{Rh}$ (SEQ ID NO:10) and (C) pure VQD$^{Rh}$TRL (SEQ ID NO:2).

Figure 29B:
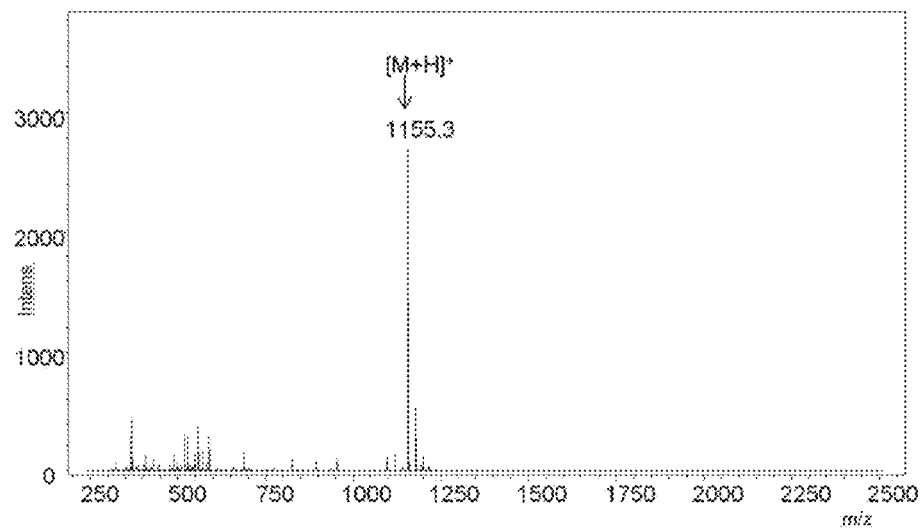

FIG. 29B illustrates the ESI-MS data of the purified product for VQD$^{Rh}$TRL (SEQ ID NO:2).

Figure 30A:
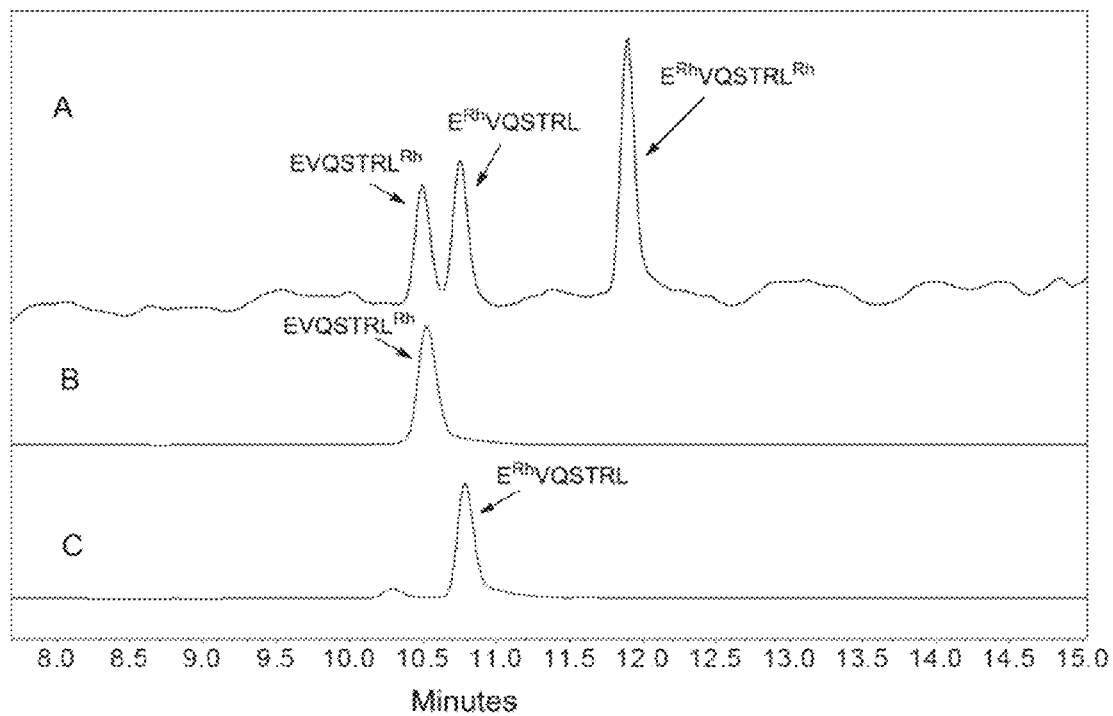

FIG. 30A illustrates the HPLC traces of (A) crude metalation (SEQ ID NOS 9, 7 and 22, respectively, in order of appearance) (B) pure EVQSTRL$^{Rh}$ (SEQ ID NO:9) and (C) pure $E^{Rh}$VQSTRL (SEQ ID NO:7).

Figure 30B:
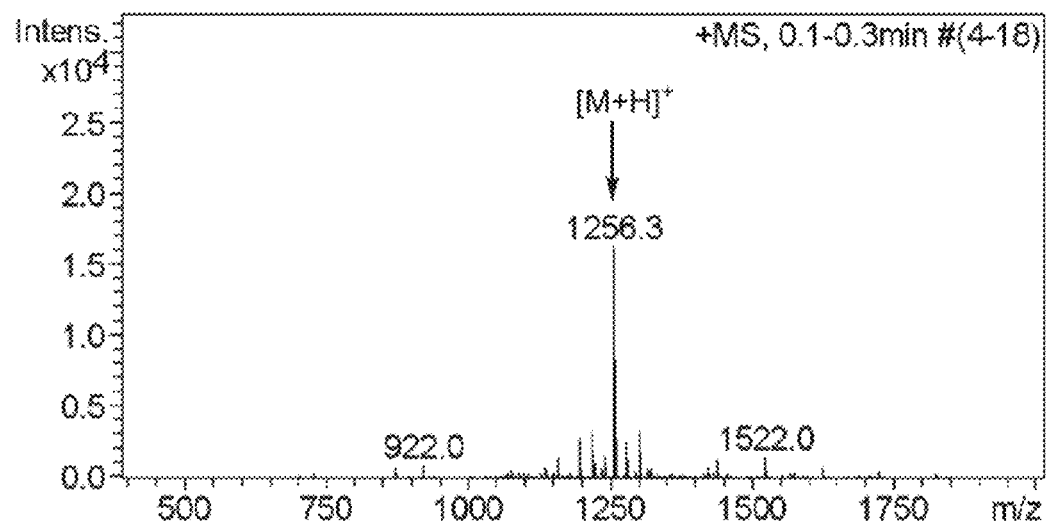

FIG. 30B illustrates the ESI-MS data of the purified product for $E^{Rh}$VQSTRL (SEQ ID NO:7).

Figure 31A:
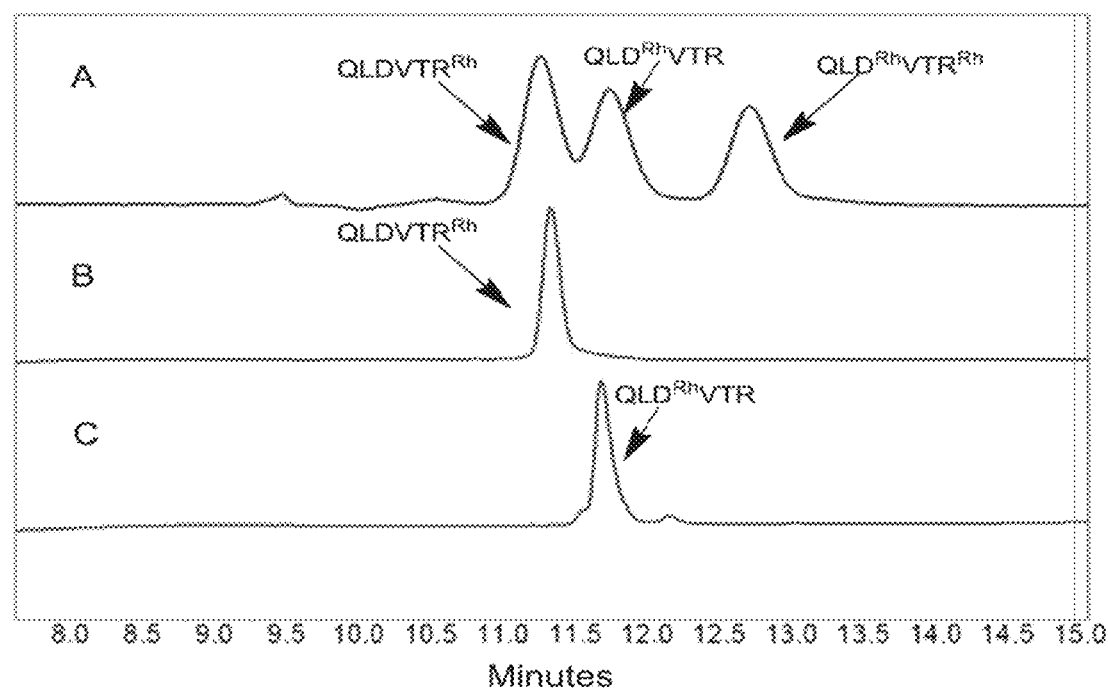

FIG. 31A illustrates the HPLC traces of (A) crude metalation (SEQ ID NOS 16, 4 and 23, respectively, in order of appearance) B) pure QLDVTR$^{Rh}$ (SEQ ID NO: 16) and (C) pure QLD$^{Rh}$VTR (SEQ ID NO:4).

Figure 31B:
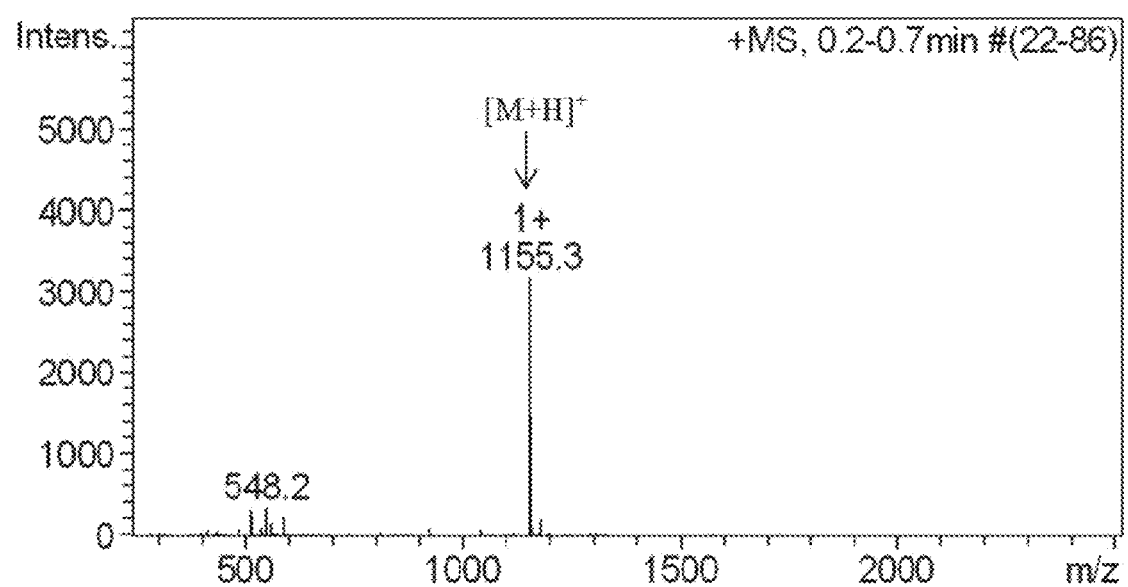

FIG. 31B illustrates the ESI-MS data of the purified product for pure QLD$^{Rh}$VTR (SEQ ID NO:4).

Figure 32A:
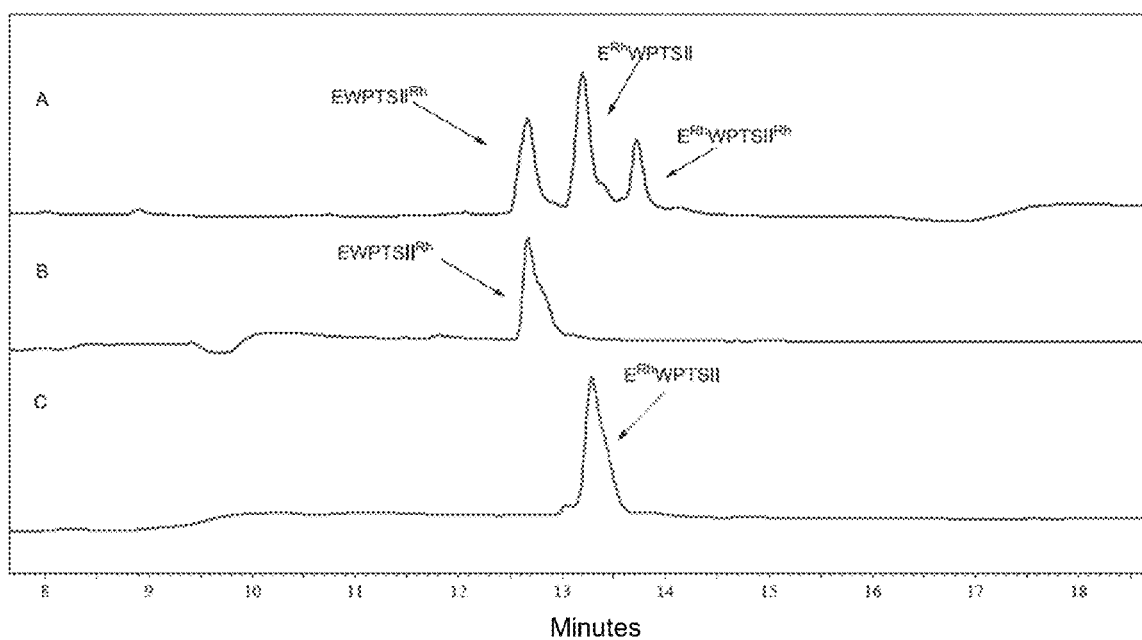

FIG. 32A illustrates the HPLC traces of (A) crude metalation (SEQ ID NOS 11, 8 and 24, respectively, in order of appearance) (B) pure B) pure EWPTSII$^{Rh}$ (SEQ ID NO:11) and (C) pure $E^{Rh}$WPTSII (SEQ ID NO:8).

Figure 32B:
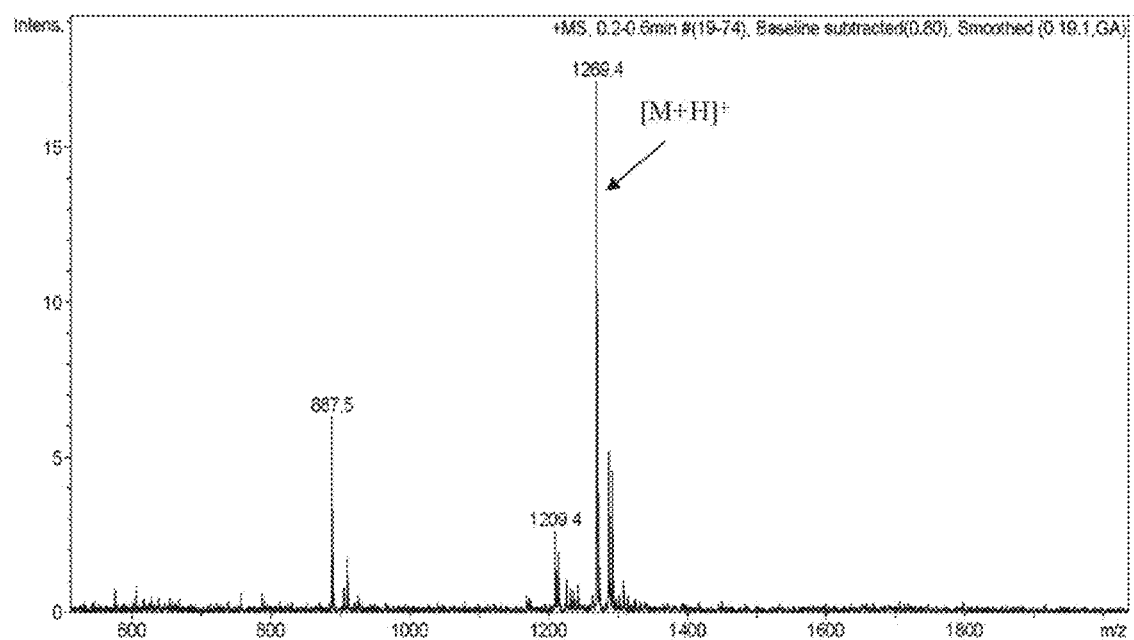

FIG. 32B illustrates the ESI-MS data of the purified product for pure $E^{Rh}$WPTSII (SEQ ID NO:8).

Figure 33A:
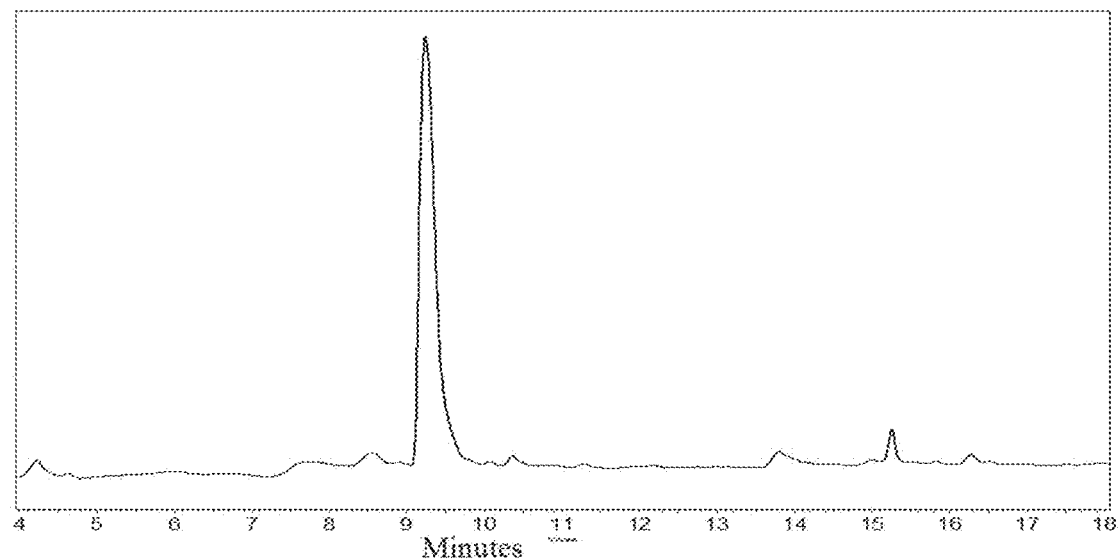
Figure 33B:
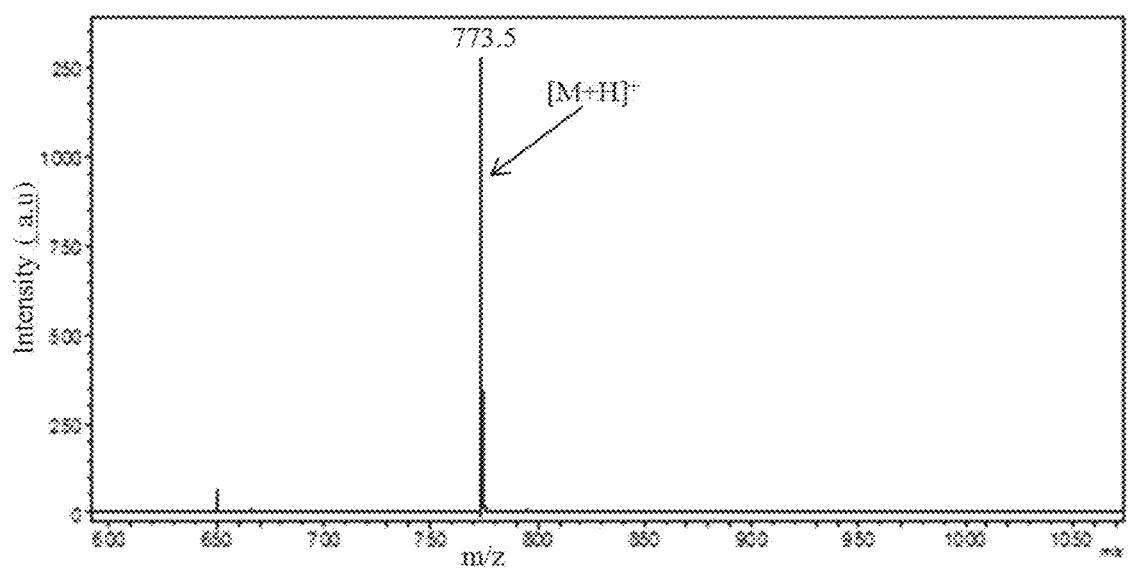

FIGS. 33A and 33B respectively illustrate the HPLC trace and MS data for the isolated peptide VQDTRL (SEQ ID NO:1).

Figure 34A:
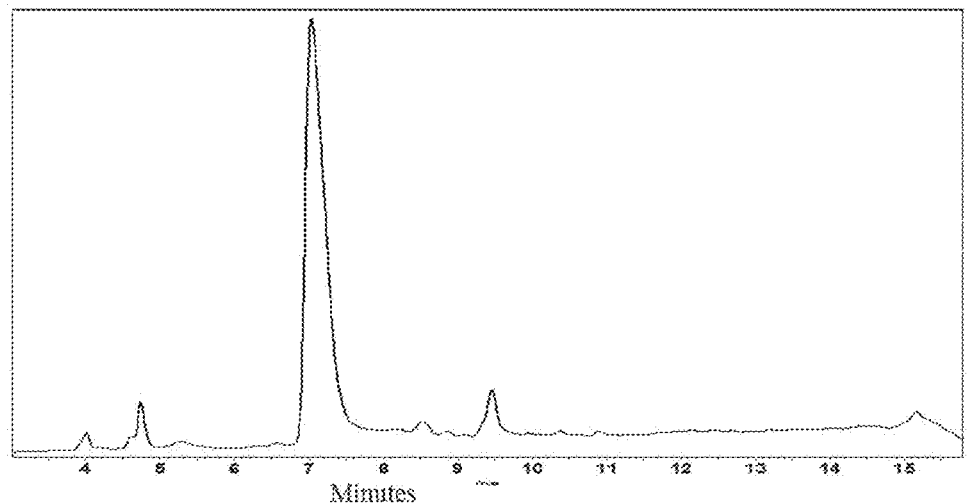
Figure 34B:
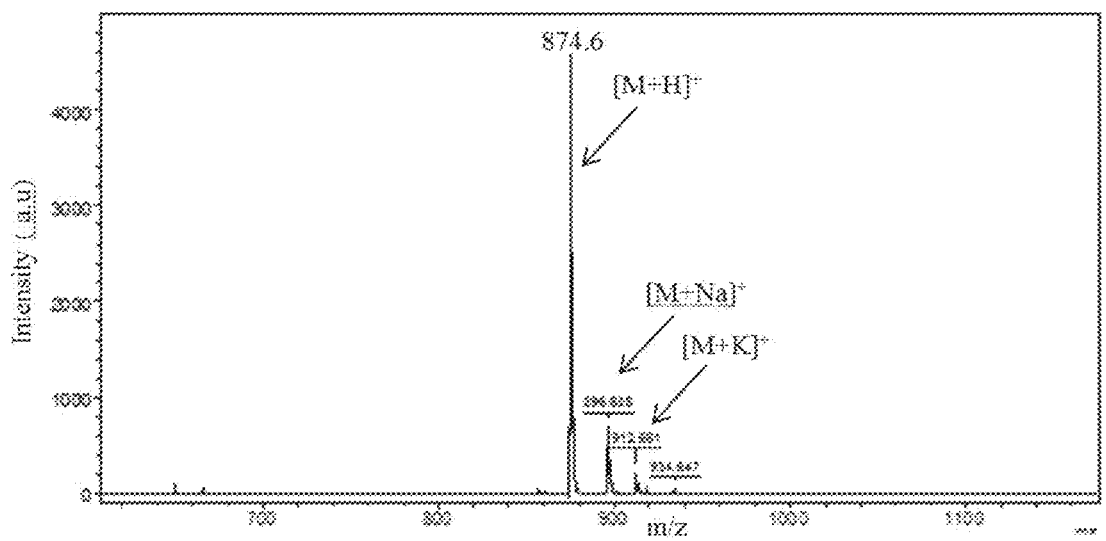

FIGS. 34A and 34B respectively illustrate the HPLC trace and MS data for the isolated peptide EVQSTRL (SEQ ID NO:6).

Figure 35A:
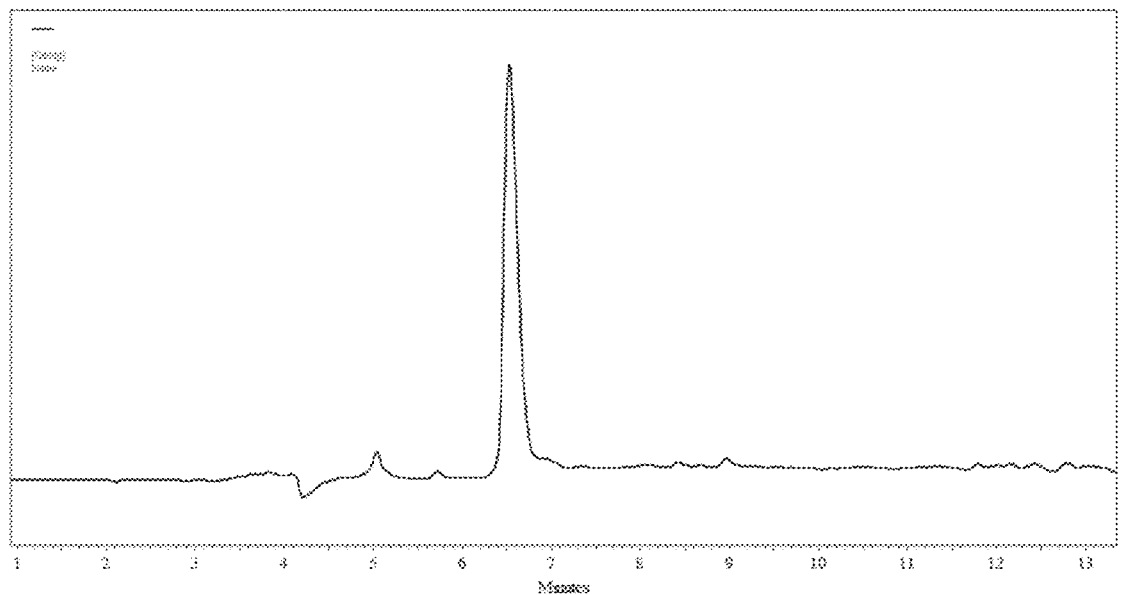
Figure 35B:
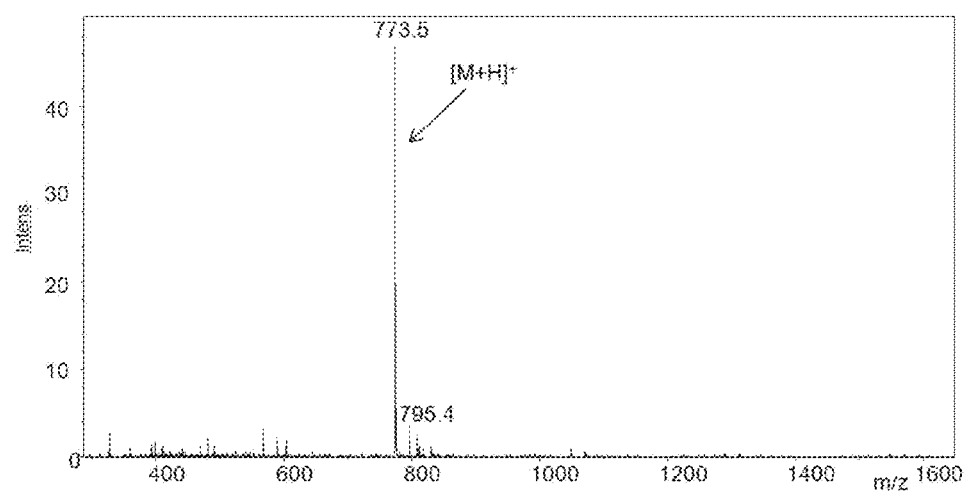

FIGS. 35A and 35B respectively illustrate the HPLC trace and MS data for the isolated peptide QLDVTR (SEQ ID NO:3).

Figure 36A:
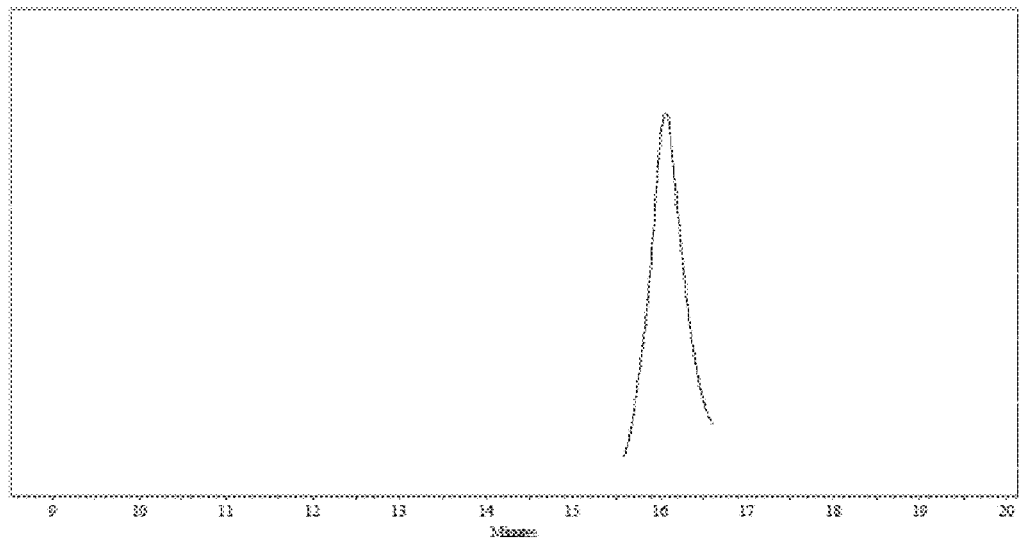
Figure 36B:
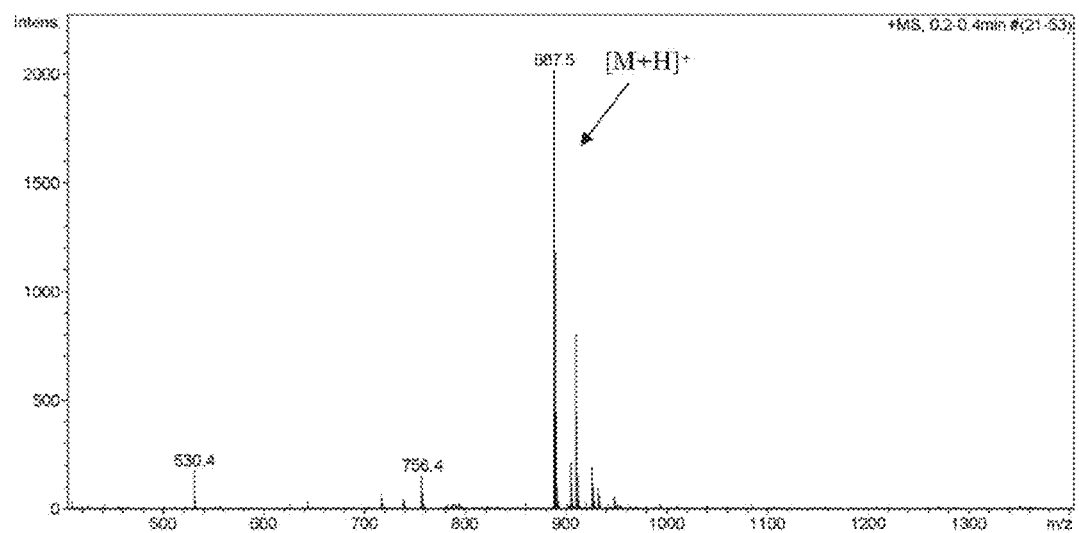

FIGS. 36A and 36B respectively illustrate the HPLC trace and MS data for isolated peptide EWPTSII (SEQ ID NO:5).

While the present disclosure is susceptible to various modifications and alternative forms, specific example embodiments have been shown in figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

The patent or application file contains at least one drawing executed in color. Copies of this patent or patent application publication with color drawing(s) will be provided by the Office upon request and payment of the necessary fee.

DESCRIPTION

The present disclosure generally relates to methods for providing protein inhibition and more particularly to methods using protein inhibitors comprising rhodium(II) complexes.

The present disclosure provides, according to certain embodiments, methods comprising introducing to a target protein a compound comprising an inhibitor covalently linked to a rhodium(II) complex and allowing the protein and compound to interact and form stabilizing secondary contacts between the rhodium(II) complex and the protein. The inhibitor covalently linked to a rhodium(II) complex may be more selective and potent than inhibitor molecules that rely on organic non-covalent assembly or inorganic coordination assembly separately.

Figure 1:
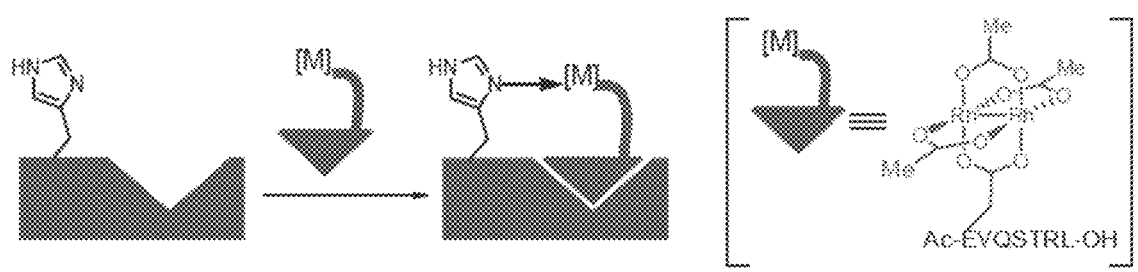
FIG. 1 is an illustration the binding mechanism of a hybrid structure.

It has previously been shown that for enzyme inhibitors, multiple weak interactions can be combined to yield polyvalent ligands with enhanced potency and specificity. The present disclosure is based in part on hybrid structures utilizing cooperative organic-inorganic binding to a target protein. FIG. 1 illustrates the binding mechanism of such a hybrid structure.

The inhibitors may be covalently linked to a rhodium(II) complex through carboxylate side chains. In general, the rhodium(II) complex is capable of forming secondary contacts with a target protein, for example, at the periphery of a protein binding interface. Such secondary contacts facilitate interaction between the inhibitor and the target protein. The dirhodium centers can interact with specific amino acid residues delivering significantly more stabilization energy (up to 5 kcal/mol) than noncovalent interactions (typically <1 kcal/mol). In certain embodiments, the rhodium(II) metallopeptide may be capable of reversible coordination chemistry across a binding interface.

Figure 2:
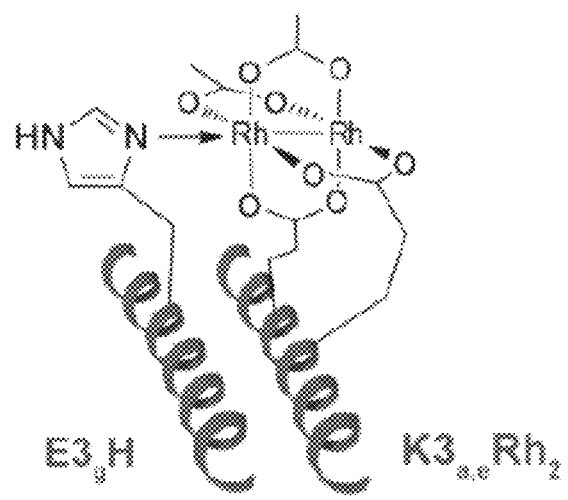
FIG. 2 is an illustration of a di-metal "pinwheel" structure. The axial coordination in E3$_g$H-K3$_{a,e}$Rh$_2$ stabilizes the coiled coil.

It is believed that to exploit reversible coordination chemistry across the binding interface, a discrete organic-inorganic complex must contain a stable organic-metal linkage, while allowing ligand exchange at the metal center in order to bind targeted side chains. Di-metal "pinwheel" structures, such as rhodium(II) tetracarboxylate, have well differentiated ligand environments containing both kinetically inert, equatorial $\kappa^2$-carboxylate ligands and kinetically labile axial ligand sites (see FIG. 2), with demonstrated capabilities to bind biologically relevant thiol and imidazole compounds in a reversible manner.

In general, inhibitors suitable for use include peptides, peptidomimentics, or a small molecule therapeutic (i.e., not peptide-based) that are capable of covalently binding to the rhodium(II) complex.

In certain embodiments, the inhibitor is a peptide that comprises a Lewis basic side chains (e.g., histidine or methionine). For example, a rhodium(II) metallopeptides may comprise Lewis basic side chains comprising glutamate ($E3_gE$) or methionine ($E3_gM$) peptides.

In certain specific embodiments, the inhibitor covalently linked to a rhodium(II) complex is capable of displacing representative peptide ligands from the PDZ domain of the cystic fibrosis transmembrane conductance regulator (CFTR)-associated ligand CAL. The PDZ domain is a family of peptide-binding PPI modules named for the first three members: PSD-95, Dlg, and ZO-1.

In certain specific embodiments, the covalently linked to a rhodium(II) complex is an inhibitor of Na+/H+ exchanger regulatory factor 1 (NHERF 1) binding to the cystic fibrosis transmembrane conductance regulator (CFTR).

To facilitate a better understanding of the present invention, the following examples of certain aspects of some embodiments are given. In no way should the following examples be read to limit, or define, the entire scope of the invention.

EXAMPLES

Rhodium(II) centers are capable of forming stabilizing secondary contacts at the periphery of a protein binding interface while examining the coiled-coil assembly of rhodium(II) metallopeptides with histidine-containing peptides. A rhodium(II) center linked to a coil at positions a and e of a heptad repeat abcdefg (See FIG. 4) would be proximal to position g of the complementary peptide, $E3_gX$. It has been found that coordination of appropriate position g side chains strongly stabilizes the coiled coil. For example, thermal denaturation of a mixture of $E3_gH$ and $K3_{a,e}Rh_2$ revealed a high melting temperature ($T_m$=66.1° C.; See FIG. 4, entry 1 and FIG. 5), in contrast to simple E3/K3 dimers and to control experiments with non-coordinating phenylalanine ($T_m$=39.5° C., FIG. 4, entry 1).

This coiled-coil stabilization reflects a specific interaction of the rhodium center. It has been shown that moving the histidine residue away from the interface, to position c, led to a drop in $T_m$ to 47.0° C. (FIG. 4, entry 8, and FIG. 5). The addition of large concentrations of imidazole, either before or after coiled-coil assembly, also led to a significant drop in melting temperature (to 46° C., FIG. 5), providing evidence for a reversible metal-ligand interaction. Finally, upon assembly with the $E3_gH$ coil, the metallopeptide $K3_{a,e}Rh_2$ exhibits a blue shift of the UV-vis absorption peak from 587 nm to 567 nm, consistent with a rhodium(II) tetracarboxylate containing axial nitrogen or sulfur ligands.

Coiled-coil assemblies with either glutamate ($E3_gE$) or methionine ($E3_gM$) peptides exhibited elevated $T_m$ values (50.2° C. and >70° C., respectively), consistent with carboxylate-rhodium or stronger thioether-rhodium interactions (FIG. 4, entries 3, 5-7). The $T_m$ values of 65-70° C. represent the most stable intermolecular coiled coils yet reported for such a short peptide (21 amino acids), similar to stabilities achieved with covalent crosslinking Insertion of cysteine at the same position, on the other hand, led to a coiled coil with decreased stability.

To extend the concept of organic-inorganic cooperatively to the discovery of potent PPI inhibitors, interactions between the CAL PDZ domain (CALP) and the cystic fibrosis transmembrane conductance regulator (CFTR) were examined. The C-terminus of CFTR interacts with several proteins (e.g. CAL, NHERF1). Despite its potential value as a target, inhibiting CALP is distinctly difficult due to its broad specificity and comparatively low baseline affinity. A screen of inverted peptide arrays was combined with in vitro fluorescence polarization measurements to identify selective CALP inhibitors. However, the potency of these inhibitors remained modest, with Ki≥1.3 µM.

The CAL PDZ domain contains several histidine residues near the peptide-binding site, making it an attractive target for a hybrid organic-inorganic approach to inhibitor design (See FIG. 6). To test the potential contributions of rhodium-based interactions to CALP inhibitor affinity, known methods were used to prepare metallopeptides based on sequences known to interact with CALP. PDZ binding requires free C-terminal carboxylates, and it was found to be convenient to metalate a peptide containing both C-terminal and side-chain carboxylates and then to isolate the side-chain-modified metallopeptide from the product mixture by HPLC (See FIG. 7).

Inhibitor equilibrium dissociation ($K_i$) constants were measured using fluorescence anisotropy to observe the displacement of a fluorescent reporter peptide (FIG. 8 and FIG. 9). The VQDTRL (SEQ ID NO:1) peptide, derived from the native target CFTR, had a weak CALP affinity. Direct incorporation of a rhodium(II) center at the aspartate side-chain carboxylate (VQD$^{Rh}$TRL (SEQ ID NO:2)) resulted in a decrease in the apparent inhibitory constant ($K_i$) relative to the parent peptide (FIG. 9A, entries 1-2), but when the new value (6.3 µM) was compared to a simple rhodium complex, $Rh_2(OAc)_4$, the improvement was not statistically significant. The apparent affinity of VQD$^{Rh}$TRL (SEQ ID NO:2) was also comparable to that of a metallopeptide derived from a non-binding, scrambled control sequence, QLD$^{Rh}$VTR (SEQ ID NO:4) (FIG. 9A, entry 4). Together, these data suggest that the effects seen with rhodium(II) addition at the P$^{-3}$ site (P$^0$=C-terminal residue) of VQDTRL (SEQ ID NO:1) are not specific.

Two metallopeptides having a site of rhodium attachment at the P$^{-6}$ were designed because it was believed that the structural analysis of the CALP domain indicated that the P$^{-6}$ position should be proximal to the His301 residue in this target (See FIG. 6). FIG. 9, entries 5-8 demonstrate that these metallopeptides exhibit statistically significant and reproducible affinity enhancement relative to controls (FIG. 9, entries 5-8). Working with a sequence (EWPTSII (SEQ ID NO:5)) carrying a glutamate side chain at the P$^{-6}$ position, metalation increased binding affinity from 65 to 1.7 µM, a ~40-fold enhancement. An even larger enhancement was seen with the sequence EVQSTRL (SEQ ID NO:6), which contains the dominant C-terminal tetrapeptide identified by array screens. The metallopeptide $E^{Rh}$VQSTRL (SEQ ID NO:7) bound with the highest affinity yet reported for CALP (0.56 µM), a 75-fold change relative to the parent peptide (FIG. 8 and FIG. 9). HSQC footprinting spectra in the presence of either the peptide or metallopeptide (supporting information) were well dispersed—confirming binding to the canonical PDZ site, with localized differences.

A CALP-H301A mutant was prepared to ascertain the role of His301 in metallopeptide affinity. This mutant binds the parent EVQSTRL (SEQ ID NO:6) with a $K_i$ value of 80 µM, only slightly (~2-fold) weaker than the wild-type protein. However, the mutant binds the metallopeptide with an apparent $K_i$ of 9.2 µM, a >16-fold loss of affinity relative to wild-type, consistent with the predicted His301-rhodium ligation.

To provide an independent demonstration of rhodium-based affinity enhancement and to establish the efficacy of rhodium metallopeptides in a more complex environment, a pulldown inhibition assay was performed using epithelial cell lysate. Relative to the non-metalated control, the metallopeptide $E^{Rh}$VQSTRL (SEQ ID NO:7) exhibits improved inhibition, demonstrating that the affinity gains carry over to a more physiological environment (FIG. 10).

As shown in FIG. 10a, Western blot of native CAL was captured from epithelial lysates, in the presence of increasing concentrations of EVQSTRL (SEQ ID NO:6) peptide with (+Rh) or without (−Rh) rhodium. Quantification reveals dose-dependent inhibition of CAL pulldown (PD) by the metalated peptide (n=3) as shown in FIG. 10b. Thus, the metalation improves inhibitor potency.

The metallopeptide $E^{Rh}$VQSTRL (SEQ ID NO:7) ($K_i$=0.56 µM) is the first reported inhibitor with sub-micromolar affinity for the CAL PDZ domain and is significantly shorter than decameric single-micromolar alternatives. In addition, comparative binding studies with the CALP-H301A mutant and with $P^{-3}$ metalated peptides indicate that rhodium mediates affinity enhancement through peripheral interactions specific to the given target binding site.

FIG. 28 shows the surface representation of the CAL PDZ domain (PDB entry 2DC2; grey) and in particular shows the interfaces associated with EVQSTRL (SEQ ID NO:6) binding (red; $\delta_{norm}$>0.2 ppm) and with the localized differences observed between the metalated and non-metalated sequences (magenta). The interface is consistent with the position of the canonical PDZ binding cleft and overlaps with previously reported binding surfaces.

Materials and Methods

Solvents and reagents were purchased from Fisher Scientific and used as received. Millipore ultra-purified water (18 MΩ) was used in all cases.

Synthesis of known compounds: The dirhodium precursor cis-Rh2(tfa)2(OAc)2,1 substrate coil peptides and catalysts K3a,eRh2 and K3g,dRh2,2 as well as the diazo reagent [2-(2-methoxyethoxy)ethoxy]ethyl (E)-4-phenyl-2-diazo-3-butenoate (1)3a were prepared and purified according to published procedures that are known in the art.

Peptide synthesis: All peptides were synthesized with an Advanced ChemTech APEX 396 Automated Multipeptide Synthesizer using standard solid-phase Fmoc protocols. Rink amide MBHA resin (AAPPTEC) or preloaded Wang resin (AAPPTEC) was used to afford C-terminal amides or carboxylates, respectively. The peptides were acetylated at the N-terminus prior to cleavage from the resin. The purification was accomplished by reverse-phase HPLC with gradients of water-acetonitrile containing 0.1% trifluoroacetic acid, and peptides were isolated by lyophilization. Analysis and purity assessment was attained by mass spectrometry and analytical HPLC.

Protein reagents: The expression vector for the CALP-H301A mutant was prepared by PCR mutagenesis using the WT vector as a template. Mutagenesis was verified by DNA sequencing. Expression and purification of the WT and mutant CAL PDZ domains were performed according to commonly described and known methods in the art. The preparation of 15N-labeled protein for NMR analysis followed known published protocols.

HPLC: HPLC was performed on a Shimadzu CBM-20A instrument with Phenomenex Jupiter 4µ Proteo 90A (250×15 mm preparative) and Phenomenex Jupiter 4µ Proteo 90A (250×4.6 mm analytical) columns. Flow rates of 8 mL/min and 1 mL/min were used for preparative and analytical columns, respectively. Analytical and preparative HPLC were performed with gradient of acetonitrile in water. Both solvents contained 0.1% trifluoroacetic acid (TFA) unless otherwise noted. Data was collected using UV-vis absorption at 220 nm and 300 nm.

Mass Spectrometry: MALDI-MS was performed on a Bruker Daltonics Autoflex MALDI-TOF/TOF mass spectrometer with CHCA matrix (10 mg/mL, Thermo Scientific Pierce). Data analysis was performed with the mMass program.

NMR: Peptide characterization: 1H spectra were recorded on Bruker 500 UltraShield™ (500 MHz) spectrometer (for EVQSTRL (SEQ ID NO:6) system) and on Oxford (400 MHz) spectrometer (for VQDTRL (SEQ ID NO:1) system). The chemical shifts (δ) are reported in units of part per million (ppm) relative to solvent peak. HSQC footprinting: 25 µM N-labeled CAL PDZ protein was also subjected to H, N heteronuclear single quantum correlation spectroscopy (HSQC) analysis, as described, except that tris(2-carboxyethyl)phosphine was omitted from the final dialysis buffers. Spectra were measured either in the presence of 125 µM EVQSTRL (SEQ ID NO:6), 45 µM Rh-EVQSTRL (SEQ ID NO:6), or no peptide, each at a final concentration of 2.5% (v/v) DMSO. HSQC backbone crosspeaks were assigned by comparison with the previously assigned CALP apo spectrum. NMR comparisons of Dirhodium attachment results to the peptides are shown in FIGS. 24 and 25. Additionally HSQC analysis and results are shown in FIGS. 26 and 27.

UV-Vis: UV-Vis spectra were recorded on Varian-Cary 50 scan UV-Vis Spectrophotometer. The spectra were acquired with 1000 nm/min scanning speed in the range of 200-750 nm, in a quartz cuvette of -cm path length. Visible absorption spectra of c are detailed in FIGS. 22 and 23.

Circular Dichroism Spectroscopy: Thermal denaturation experiments (−5-105° C. with a gradient of 1° C./min) were performed on a Jasco-J810 spectropolarimeter with a Peltier temperature controller (Jasco PTC423S). Solutions of 1:1 E3-peptide and K3-metallopeptide (both components 100 or 33 µM) in aqueous buffer in a 0.1 cm sealed cell were analyzed, and ellipticity data were acquired at 222 nm (red data points, S-5). When imidazole additive was utilized, ellipticity data were acquired at 225 nm. Temperature denaturation curves were fit to a two-state unfolding model and plotted (black line, S-5) as fraction unfolded vs. temperature as described previously by Lavigne et al.8 Error associated with the non-linear least squared-determined Tm was determined using the freely available "Solver Statistics" macro for Microsoft Excel. The representative studies of the thermal denaturation of the Dirhodium peptide assemblies are shown in FIGS. 11-19.

Protein binding studies: Fluorescence anisotropy inhibition binding assays were performed using standard procedures. Briefly, wells were prepared containing 1.8 μM (WT) or 5.5 μM (H301A) CAL PDZ protein, 30 nM fluorescein-labeled iCAL36 reporter (Tufts University Core Facility), and varying concentrations of inhibitor peptides (VQDTRL (SEQ ID NO:1) and EVQSTRL (SEQ ID NO:6), with and without rhodium side-chain modification). Following equilibration, fluorescence anisotropy values were determined using a Tecan Infinite M1000 plate reader (n=3). Inhibitor equilibrium dissociation (Ki) constants were estimated as described. DMSO and rhodium(II) acetate were used as negative controls for unlabeled and labeled peptides, respectively.

Capture inhibition assays: To determine the ability of inhibitor peptides to displace the interactions of full-length CAL in the presence of the epithelial-cell proteome, a capture inhibition assay was developed. Briefly, using published methods a biotin-conjugated peptide "bait" sequence (BT-iCAL36) was immobilized on streptavidin beads and incubated with clarified lysates of CFBE4lo− cells to capture full-length CAL in the presence of cellular proteins. For the inhibition assay used here, capture was performed in the presence of a dilution series of metalated or non-metalated EVQSTRL (SEQ ID NO:6) inhibitor peptides. Beads were washed and eluted, and bound proteins were separated by SDS-PAGE and immunoblotted using an α-CAL antibody. Band intensities were separately quantified and averaged (n=3).

Synthetic Procedures.

General procedure for synthesis of CFTR-derived metallopeptides: Example synthesis of VQD$^{Rh}$TRL (SEQ ID NO:2): The peptide VQDTRL (SEQ ID NO:1) (15.0 mg, 19.4 μmol) and Rh2(tfa)(OAc)3 (10.1 mg, 20.4 μmol) were charged into a 1-dram vial equipped with a stir bar. A solution of MES buffer (2-(N-morpholino)ethanesulfonic acid, 19.4 mL, 0.1 M aq soln, pH 4.9) was added. The reaction was heated at 50° C. overnight, after which all reactants were consumed based on HPLC analysis. The resulting mixture of dirhodium-peptide complexes were purified by direct injection of the reaction mixture onto a preparative HPLC column. The metallopeptide bound through the C-terminal carboxylate eluted first, followed by the desired aspartate-bound metallopeptide, which was isolated by lyophilization to afford a fluffy light blue powder (8.35 mg, 46% yield). Smaller amounts of the later-eluting bis-dirhodium metallopeptide could also be isolated. Analysis and purity assessment was attained by ESI-MS and analytical HPLC. The site of metalation was determined by 1H NMR spectroscopy on the basis of chemical shifts of protons proximal to the bound dirhodium. Dirhodium attachment resulted in discernible changes to one leucine Hδ methyl (from 0.87 ppm to 0.65 ppm, Δδ1H ca. −0.22 ppm) in the C-terminal bound product VQDTRL$^{Rh}$ (SEQ ID NO:10), and to the aspartate Hβ methylene (from 2.81 ppm to 2.69 ppm, Δδ1H ca. −0.12 ppm) in the side-chain-bound metallopeptide, VQD$^{Rh}$TRL (SEQ ID NO:2) and as shown in FIGS. 20 and 21.

Additional analysis and purity assessments of the CFTR-derived metallopeptide assemblies are shown in FIGS. 29A, 29B, 30A, 30B, 31A, 31B, 32A, 32B, 33A, 33B, 34A, 34B, 35A, 35B, 36A, and 36B.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A method comprising:
   introducing to a target protein a compound comprising a peptide ligand from the PDZ domain of a cystic fibrosis transmembrane conductance regulator (CFTR)-associated ligand wherein the peptide ligand is covalently linked to a rhodium(II) complex and wherein the compound binds to the target protein and form stabilizing secondary contacts between the rhodium(II) complex and the target protein.

2. A method comprising:
   introducing to a target protein a compound comprising a peptide covalently linked to a rhodium(II) complex, wherein the peptide comprises a sequence selected from the group consisting of SEQ ID NO: 7, SEQ ID NO: 8, and SEQ ID NO: 15, and wherein the compound binds to the target protein and forms stabilizing secondary contacts between the rhodium(II) complex and the target protein.

3. The method of claim 2, wherein the sequence is SEQ ID NO: 7.

4. The method of claim 2, wherein the sequence is SEQ ID NO: 8.

5. The method of claim 2, wherein the sequence is SEQ ID NO: 15.

* * * * *